United States Patent
Lindström et al.

(10) Patent No.: US 11,219,618 B2
(45) Date of Patent: Jan. 11, 2022

(54) PYRIDYLPYRIDONE COMPOUNDS

(71) Applicant: Sprint Bioscience AB, Huddinge (SE)

(72) Inventors: Johan Lindström, Huddinge (SE); Rickard Forsblom, Huddinge (SE); Tobias Ginman, Huddinge (SE); Fredrik Rahm, Huddinge (SE); Jenny Viklund, Huddinge (SE)

(73) Assignee: Sprint Bioscience AB, Huddinge (SE)

( * ) Notice: Subject to any disclaimer, the term of this patent is extended or adjusted under 35 U.S.C. 154(b) by 0 days.

(21) Appl. No.: 16/639,895

(22) PCT Filed: Aug. 23, 2018

(86) PCT No.: PCT/EP2018/072788
§ 371 (c)(1),
(2) Date: Feb. 18, 2020

(87) PCT Pub. No.: WO2019/038387
PCT Pub. Date: Feb. 28, 2019

(65) Prior Publication Data
US 2020/0289496 A1 Sep. 17, 2020

(30) Foreign Application Priority Data
Aug. 23, 2017 (EP) .................................... 17187544

(51) Int. Cl.
| | |
|---|---|
| *A61K 31/4545* | (2006.01) |
| *A61K 31/44* | (2006.01) |
| *A61K 31/4412* | (2006.01) |
| *A61K 31/444* | (2006.01) |
| *A61K 31/495* | (2006.01) |
| *A61K 31/5355* | (2006.01) |
| *A61K 31/69* | (2006.01) |
| *C07D 213/69* | (2006.01) |
| *C07D 213/75* | (2006.01) |
| *C07D 241/04* | (2006.01) |
| *C07D 401/04* | (2006.01) |
| *C07D 401/14* | (2006.01) |
| *C07D 409/14* | (2006.01) |
| *C07D 413/04* | (2006.01) |
| *C07D 413/14* | (2006.01) |
| *C07F 5/02* | (2006.01) |

(52) U.S. Cl.
CPC .......... *A61K 31/4545* (2013.01); *A61K 31/44* (2013.01); *A61K 31/444* (2013.01); *A61K 31/4412* (2013.01); *A61K 31/495* (2013.01); *A61K 31/5355* (2013.01); *A61K 31/69* (2013.01); *C07D 213/69* (2013.01); *C07D 213/75* (2013.01); *C07D 241/04* (2013.01); *C07D 401/04* (2013.01); *C07D 401/14* (2013.01); *C07D 409/14* (2013.01); *C07D 413/04* (2013.01); *C07D 413/14* (2013.01); *C07F 5/027* (2013.01)

(58) Field of Classification Search
None
See application file for complete search history.

(56) References Cited

U.S. PATENT DOCUMENTS

2013/0331382 A1* 12/2013 Hubbard ............. A61K 31/541
514/227.8

FOREIGN PATENT DOCUMENTS

| WO | WO 03/099808 A1 * | 12/2003 | ............. A61K 31/44 |
| WO | WO 2012/085815 A1 | 6/2012 | |
| WO | WO 2015/108861 A1 | 7/2015 | |
| WO | WO 2017/140841 A1 | 8/2017 | |
| WO | WO 2017/140843 A1 | 8/2017 | |

OTHER PUBLICATIONS

International Search Report and Written Opinion of the International Searching Authority for PCT/EP2018/072788 (dated 2018).*

* cited by examiner

Primary Examiner — Zinna Northington Davis
(74) Attorney, Agent, or Firm — Goodwin Procter LLP

(57) ABSTRACT

The invention provides novel pyridylpyridone compounds of formula (I), pharmaceutical compositions containing such compounds, and methods for using such compounds in treatment of diseases including cancer, type II diabetes, inflammatory disease, autoimmune diseases, neurodegenerative disorders, cardiovascular disorders and viral infections; wherein $R^1$, $R^2$, $R^3$ and X are as defined in the specification.

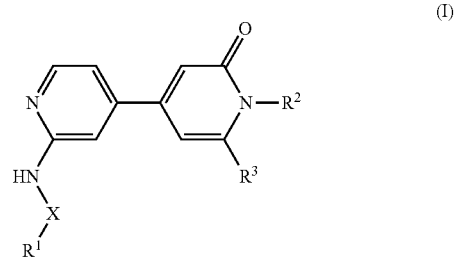

(I)

17 Claims, No Drawings

PYRIDYLPYRIDONE COMPOUNDS

CROSS-REFERENCE TO RELATED APPLICATIONS

This application is a § 371 national phase of International Application No. PCT/EP2018/072788, filed on Aug. 23, 2018, which claims the benefit of European Patent Application No. 17187544.6, filed on Aug. 23, 2017, which applications are incorporated by reference herein.

FIELD OF THE INVENTION

The invention provides novel pyridylpyridone compounds of formula (I), pharmaceutical compositions containing such compounds, and methods for using such compounds in treatment of diseases including cancer and type II diabetes.

BACKGROUND OF THE INVENTION

Enzymes belonging to the family of phosphatidylinositide 3-kinases (PI3K) are regulators of several important cellular events. The family consists of three classes, I, II and III and while the Class I group has been an interesting drug target for many years, Class II and III are less exploited. The PI3K Class III, vacuolar protein sorting 34 (Vps34, PIK3C$_3$) forms a heterodimer with its regulatory subunit p150 (Vps15) and this dimer takes part in several complexes regulating vesicular trafficking events such as autophagy, endocytosis, exocytosis and micropinocytosis (Amaravadi et al. Clin Cancer Res. 2011, 17:654-666; Carpentier et al. 2013, Traffic). The enzyme is responsible for phosphorylation of phosphatidylinositol (PI) to phosphatidylinositol (3)-phosphate (PI3P). The ligand binding to PX and FYVE domains results in recruiting and delocalization of these effector proteins that lead to vesicular formation, elongation and movement (Backer et al. J Biochem. 2008, 410:1-17).

Autophagy is a catabolic process where cellular components are targeted for degradation by enclosing them in double-membrane vesicles, auto-phagosomes that are fused with the protease-containing lysosomes. This is a mean for the cell to handle damaged organelles and misfolded proteins and by that maintain cellular function. The pathway is also a way of recirculating cellular content into new building blocks (Boya et al, Nat Cell Biol 2013, 15; 713-720). Autophagy is a cellular response to stressful conditions as nutrient deprivation, acidosis and hypoxia but also to drug treatment.

Therefore, autophagy inhibition is a means to potentiate cancer drugs and resensitize drug resistant tumors (Nagelkerke et al, Semin Cancer Biol 2014, 31; 99-105). Most advanced tumors show a high upregulation of autophagic flux (Leone et al. Trends in Endocrin Metab 2013, 24; 209-217). An established marker for studying autophagic flux is the detection of autophagic puncta in the form of lipidated LC3 protein on the autophagosome. Inhibition of Vps34 results in the inhibition of autophagy as measured by LC3 redistribution into puncta (Dowdle et al., Nat Cell Biol 2014, 16; 1069-79).

As recently described, ablation of the regulatory subunit p150 leads to increased insulin sensitivity in vivo due to decreased insulin receptor internalization (Nemazanyy, Nature Commun., 2015, 6:8283). A kinase dead heterozygous animal model confirms this result with increased glucose tolerance and increased insulin sensitivity (WO2013076501).

Several disease states could benefit from Vps34 inhibition including cancer, inflammatory diseases, autoimmune diseases, neurodegenerative disorders, cardiovascular disorders, type II diabetes and viral infections (Reviewed in Rubinsztein et al, Nat Rev 2012, 11; 709-730). Cancer forms that would benefit from Vps34 inhibition include, but are not limited to, breast cancer, such as triple negative breast cancer, bladder cancer, liver cancer, cervical cancer, pancreatic cancer, leukemia, lymphoma, renal cancer, colon cancer, glioma, prostate cancer, ovarian cancer, melanoma, and lung cancer as well as hypoxic tumors. There is thus a need for novel and potent inhibitors of Vps34.

Previous disclosures describing Vps34 inhibitors in use to affect diseases include WO2015150555; WO2015150557; WO2015108861; WO2015108881; WO2012085815; WO2012085244; WO2013190510; Farkas, J. Biol. Chem., 2011 286(45) 38904-12.

DESCRIPTION OF THE INVENTION

An object of the invention is to provide novel and potent inhibitors of Vps34. Another object of the invention is to provide novel and potent inhibitors of Vps34 that may be used for treating cancer and other diseases such as type II diabetes.

According to one aspect of the invention, there is provided a compound of Formula (I)

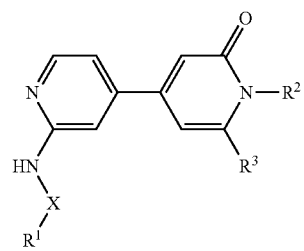

wherein
X is C=O or a bond;
$R^1$ is selected from H, $C_1$-$C_3$alkyl, $C_1$-$C_3$haloalkyl, $C_1$-$C_3$alkoxy$C_1$-$C_3$alkyl, $C_3$-$C_6$cycloalkyl, $C_3$-$C_6$cyclohaloalkyl, $C_1$-$C_3$alkoxy, $C_1$-$C_3$haloalkoxy, $C_3$-$C_6$cycloalkoxymethyl, N—$C_1$-$C_3$alkylamino, N,N-di$C_1$-$C_3$alkylamino, 1-pyrrolidinyl, 1-piperidinyl and 1-azetidinyl, provided that when $R^1$ is $C_1$-$C_3$alkoxy, $C_1$-$C_3$haloalkoxy, N—$C_1$-$C_3$alkylamino N,N-di$C_1$-$C_3$alkylamino, 1-pyrrolidinyl, 1-piperidinyl or 1-azetidinyl, then X is C=O;
$R^2$ is selected from hydrogen, $C_1$-$C_3$haloalkyl and $C_1$-$C_3$alkyl;
$R^3$ is selected from A, phenyl and monocyclic heteroaryl, said phenyl and said heteroaryl being optionally substituted with one or more of $R^4$, $R^5$, $R^6$ and $R^7$;
$R^4$, $R^5$, $R^6$ and $R^7$ are independently selected from halo, $C_1$-$C_6$alkyl, $C_3$-$C_6$cycloalkyl, $C_1$-$C_6$alkoxy, $C_1$-$C_3$haloalkoxy, N,N-di$C_1$-$C_3$alkylamino, N—$C_1$-$C_3$alkylamino, 1-azetidinyl, $C_1$-$C_6$haloalkyl, amino, NHSO$_2$R$^8$, SO$_2$R$^9$ and hydroxy;
$R^8$ is $C_1$-$C_3$haloalkyl or $C_1$-$C_3$alkyl;
$R^9$ is selected from $R^{10}$, $C_1$-$C_6$alkyl, amino, N—$C_1$-$C_3$alkylamino, N,N-di$C_1$-$C_3$alkylamino and $C_1$-$C_3$alkoxy$C_1$-$C_3$alkyl, said $C_1$-$C_6$alkyl and said $C_1$-$C_3$alkoxy$C_1$-$C_3$alkyl being optionally substituted with one $R^{10}$ and/or one or more halo;

$R^{10}$ is selected from phenyl, monocyclic heteroaryl, $C_3$-$C_6$cycloalkyl, heterocyclyl, each optionally substituted with one or more $R^{11}$;

$R^{11}$ is selected from halo, $C_1$-$C_3$alkoxy$C_1$-$C_3$alkyl, amino, N—$C_1$-$C_3$alkylamino, N,N-di$C_1$-$C_3$alkylamino, $C_1$-$C_3$haloalkoxy, $C_1$-$C_3$alkoxy, $C_3$-$C_6$cycloalkyl, $C_1$-$C_3$haloalkyl and $C_1$-$C_3$alkyl;

A represents

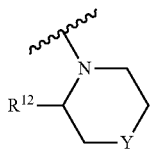

$R^{12}$ is selected from hydrogen, halo, $COR^{13}$, $C_1$-$C_6$alkyl, $C_1$-$C_3$alkoxy$C_1$-$C_3$alkyl, $C_1$-$C_6$alkoxy, $C_3$-$C_6$cycloalkyl, $C_1$-$C_3$cyanoalkyl, $C_1$-$C_3$haloalkyl;

$R^{13}$ is selected from $C_1$-$C_3$alkoxy, N—$C_1$-$C_3$alkylamino, N,N-di$C_1$-$C_3$alkylamino, 1-pyrrolidinyl, 1-piperidinyl and 1-azetidinyl;

Y represents $CH_2$, S, SO, $SO_2$, $NR^{14}$, $NCOR^9$, $NCOOR^{15}$, $NSO_2R^9$, $NCOCH_2R^9$, O, or a bond;

$R^{14}$ is selected from H, $C_1$-$C_3$haloalkyl, $C_1$-$C_3$alkoxy$C_1$-$C_3$alkyl, $C_1$-$C_3$alkyl, $C_3$-$C_6$cycloalkyl;

$R^{15}$ is selected from $R^{10}$, $C_1$-$C_6$alkyl and $C_1$-$C_3$alkoxy$C_1$-$C_3$alkyl, said $C_1$-$C_6$alkyl and said $C_1$-$C_3$alkoxy$C_1$-$C_3$alkyl being optionally substituted with one $R^{10}$ and/or one or more halo;

or a pharmaceutically acceptable salt, or pharmaceutically acceptable salts thereof.

According to one embodiment of this aspect of the invention, $R^2$ is hydrogen or $C_1$-$C_3$alkyl, such as hydrogen or methyl, such as hydrogen.

According to one embodiment of this aspect of the invention, $R^1$ is selected from H, $C_1$-$C_3$alkyl, $C_1$-$C_3$alkoxy, $C_1$-$C_3$haloalkoxy, $C_1$-$C_3$alkoxy$C_1$-$C_3$alkyl, N,N-di$C_1$-$C_3$alkylamino, 1-pyrrolidinyl and $C_3$-$C_6$cycloalkyl.

According to one embodiment of this aspect, $R^1$ is selected from H, methyl, methoxy, methoxymethyl, N,N-dimethylamino, 1-pyrrolidinyl and cyclopropyl.

According to one embodiment of this aspect of the invention, $R^1$ is selected from H, methyl, methoxymethyl, N,N-dimethylamino, 1-pyrrolidinyl and cyclopropyl.

According to one embodiment of this aspect of the invention, $R^3$ is selected from A, phenyl and monocyclic heteroaryl selected from pyridyl, thienyl, furyl, pyrimidinyl and pyrazolyl, wherein said phenyl and said heteroaryl are optionally substituted with $R^4$ and/or $R^5$.

According to one embodiment of this aspect of the invention, $R^3$ is selected from A, phenyl and pyridyl, wherein said phenyl and said pyridyl are optionally and independently substituted with $R^4$ and/or $R^5$.

According to one embodiment of this aspect of the invention, $R^4$, $R^5$, $R^6$ and $R^7$ are independently selected from fluoro, chloro, $C_1$-$C_3$alkyl, $C_3$-$C_6$cycloalkyl, $C_1$-$C_3$fluoroalkyl and $SO_2R^9$.

According to one embodiment of this aspect of the invention, Y represents $CH_2$, $NSO_2R^9$, O or a bond.

According to one embodiment of this aspect of the invention, Y represents $CH_2$, O or a bond.

According to one embodiment of this aspect of the invention, $R^{12}$ is selected from hydrogen, $C_1$-$C_3$alkyl, $C_1$-$C_3$alkoxy$C_1$-$C_3$alkyl, $C_1$-$C_3$haloalkyl and $C_3$-$C_6$cycloalkyl.

According to one embodiment of this aspect of the invention, $R^{12}$ is selected from hydrogen, $C_1$-$C_3$alkyl, $C_1$-$C_3$haloalkyl and $C_3$-$C_6$cycloalkyl.

According to one embodiment of this aspect of the invention, $R^9$ is selected from $R^{10}$, N,N-di$C_1$-$C_3$alkylamino and methoxy$C_1$-$C_3$alkyl, said $C_1$-$C_3$alkyl being optionally substituted with one $R^{10}$.

According to one embodiment of this aspect of the invention, $R^{10}$ is selected from phenyl, pyridyl, imidazolyl, isoxazolyl, oxazolyl, cyclopropyl, cyclopentyl, pyrrolidinyl, tetrahydrofuryl, each optionally substituted with one or more methyl and/or fluoro.

According to one embodiment of this aspect of the invention, $R^3$ is selected from

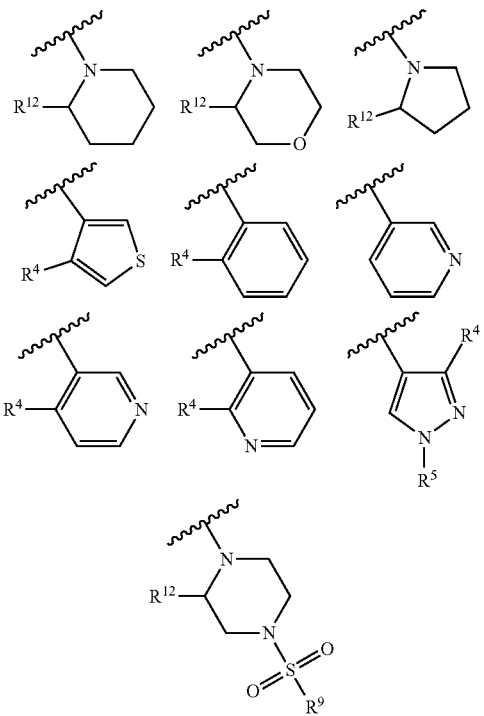

According to one embodiment of this aspect of the invention, $R^3$ is selected from

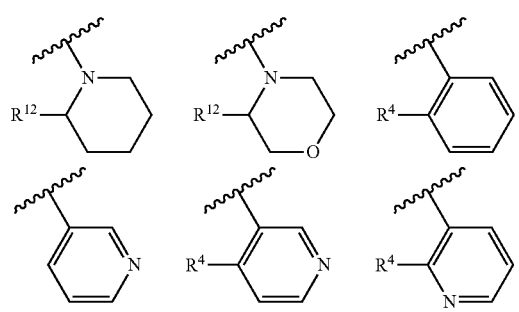

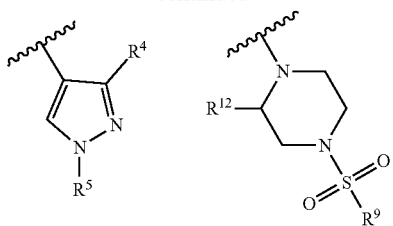

According to one embodiment of this aspect of the invention, $R^3$ is selected from

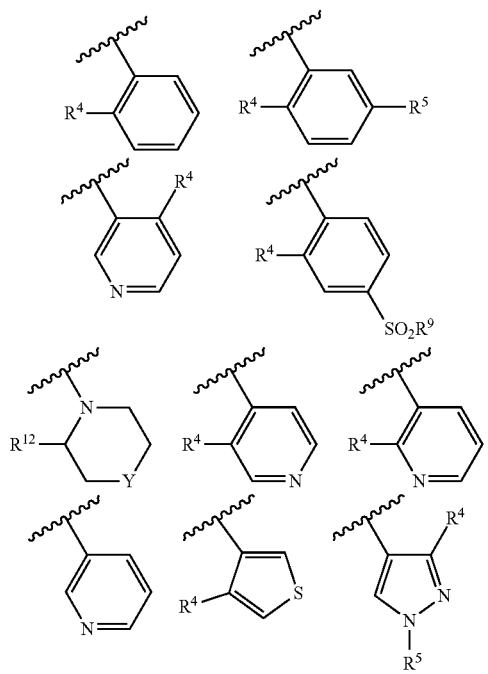

According to one embodiment of this aspect of the invention, $R^3$ is selected from

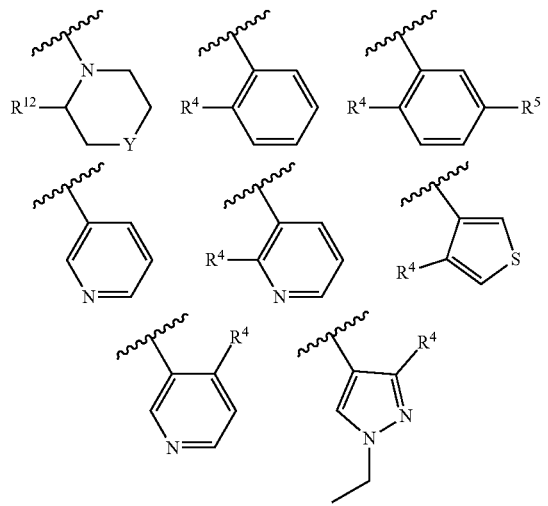

wherein Y is selected from CH2, O and a bond;
$R^4$ is selected from $CF_3$, chloro, cyclopropyl and methyl;
$R^5$ is fluoro; and
$R^{12}$ is selected from hydrogen, cyclopropyl, methyl, 1-methoxy-1-methyl-ethyl and $CF_3$.

According to one embodiment of this aspect of the invention, $R^3$ is selected from

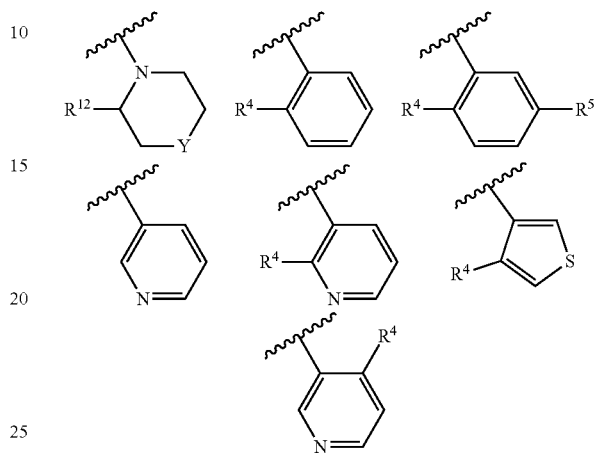

wherein Y is selected from $CH_2$, O and a bond;
$R^4$ is selected from $CF_3$, chloro, cyclopropyl and methyl;
$R^5$ is fluoro; and
$R^{12}$ is selected from hydrogen, cyclopropyl, methyl and $CF_3$.

According to one embodiment of this aspect of the invention,
$R^3$ is selected from

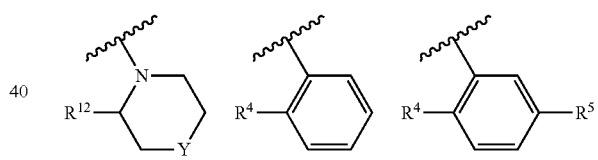

wherein Y is selected from $CH_2$ and O;
$R^4$ is selected from $CF_3$, chloro cyclopropyl and chloro;
$R^5$ is fluoro; and
$R^{12}$ is $CF_3$ and cyclopropyl.

According to one embodiment of this aspect of the invention,
$R^1$ is selected from H, methyl, methoxy, methoxymethyl, N,N-dimethylamino, 1-pyrrolidinyl and cyclopropyl;
$R^2$ is hydrogen; and
$R^3$ is selected from

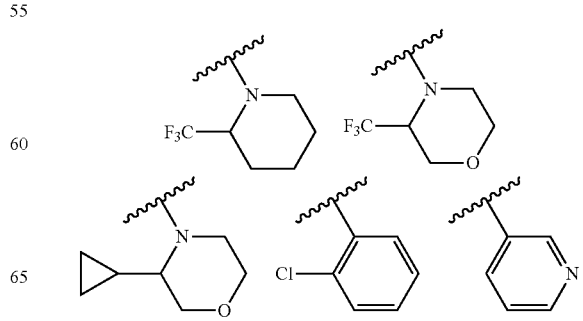

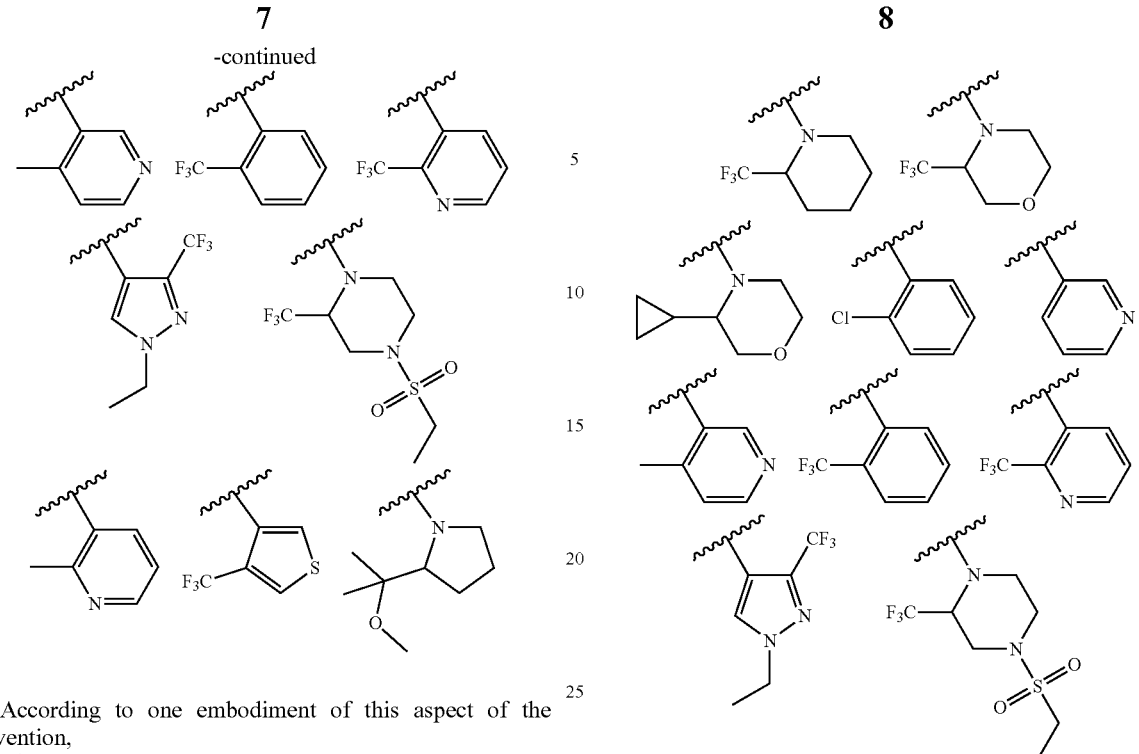

According to one embodiment of this aspect of the invention,

R¹ is selected from H, methyl, methoxy, methoxymethyl, N,N-dimethylamino, 1-pyrrolidinyl and cyclopropyl;

R² is hydrogen; and

R³ is selected from

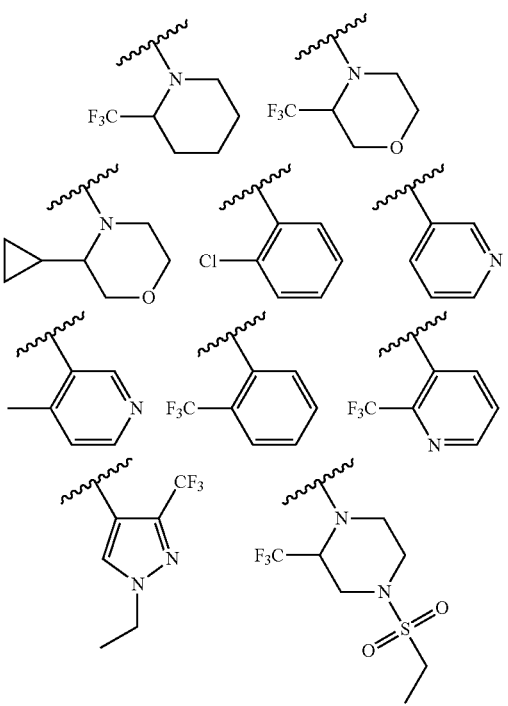

According to one embodiment of this aspect of the invention,

R¹ is selected from H, methyl, methoxymethyl N,N-dimethylamino, 1-pyrrolidinyl and cyclopropyl;

R² is hydrogen; and

R³ is selected from

According to one embodiment of this aspect of the invention, said compound is

N-[4-[2-(2-chlorophenyl)-6-oxo-1H-pyridin-4-yl]-2-pyridyl]acetamide;

4-(2-Amino-4-pyridyl)-6-(3-pyridyl)-1H-pyridin-2-one;

4-(2-Amino-4-pyridyl)-6-(2-chlorophenyl)-1H-pyridin-2-one;

N-[4-[2-(2-chlorophenyl)-6-oxo-1H-pyridin-4-yl]-2-pyridyl]-2-methoxy-acetamide;

N-[4-[2-oxo-6-[2-(trifluoromethyl)-1-piperidyl]-1H-pyridin-4-yl]-2-pyridyl]acetamide;

N-[4-[2-oxo-6-[2-(trifluoromethyl)-1-piperidyl]-1H-pyridin-4-yl]-2-pyridyl]cyclopropanecarboxamide;

N-[4-[2-oxo-6-[3-(trifluoromethyl)morpholin-4-yl]-1H-pyridin-4-yl]-2-pyridyl]acetamide;

methyl N-[4-[2-(2-chlorophenyl)-6-oxo-1H-pyridin-4-yl]-2-pyridyl]carbamate;

methyl N-[4-[2-[1-ethyl-3-(trifluoromethyl)pyrazol-4-yl]-6-oxo-1H-pyridin-4-yl]-2-pyridyl]carbamate;

methyl N-[4-[2-oxo-6-[2-(trifluoromethyl)-3-pyridyl]-1H-pyridin-4-yl]-2-pyridyl]carbamate;

methyl N-[4-[2-oxo-6-[2-(trifluoromethyl)phenyl]-1H-pyridin-4-yl]-2-pyridyl]carbamate;

N-[4-[2-oxo-6-[2-(trifluoromethyl)phenyl]-1H-pyridin-4-yl]-2-pyridyl]acetamide;

N-[4-[2-(4-methyl-3-pyridyl)-6-oxo-1H-pyridin-4-yl]-2-pyridyl]acetamide;

N-[4-[2-oxo-6-[2-(trifluoromethyl)-3-pyridyl]-1H-pyridin-4-yl]-2-pyridyl]acetamide;

N-[4-[2-[1-ethyl-3-(trifluoromethyl)pyrazol-4-yl]-6-oxo-1H-pyridin-4-yl]-2-pyridyl]acetamide;

methyl N-[4-[2-oxo-6-[3-(trifluoromethyl)morpholin-4-yl]-1H-pyridin-4-yl]-2-pyridyl]carbamate;

methyl N-[4-[2-oxo-6-[2-(trifluoromethyl)-1-piperidyl]-1H-pyridin-4-yl]-2-pyridyl]carbamate;

N-[4-[2-(3-cyclopropylmorpholin-4-yl)-6-oxo-1H-pyridin-4-yl]-2-pyridyl]acetamide;

N-[4-[2-[4-ethylsulfonyl-2-(trifluoromethyl)piperazin-1-yl]-6-oxo-1H-pyridin-4-yl]-2-pyridyl]acetamide;

N-[4-[2-(2-methyl-3-pyridyl)-6-oxo-1H-pyridin-4-yl]-2-pyridyl]acetamide;

N-[4-[2-oxo-6-[4-(trifluoromethyl)-3-thienyl]-1H-pyridin-4-yl]-2-pyridyl]acetamide;

1,1-Dimethyl-3-[4-[2-oxo-6-[2-(trifluoromethyl)phenyl]-1H-pyridin-4-yl]-2-pyridyl]urea;

N-[4-[2-oxo-6-[2-(trifluoromethyl)phenyl]-1H-pyridin-4-yl]-2-pyridyl]pyrrolidine-1-carboxamide; or N-[4-[2-[2-(1-methoxy-1-methyl-ethyl)pyrrolidin-1-yl]-6-oxo-1H-pyridin-4-yl]-2-pyridyl]acetamide.

According to one embodiment of this aspect of the invention, said compound is 4-(2-Amino-4-pyridyl)-6-(3-pyridyl)-1H-pyridin-2-one;

4-(2-Amino-4-pyridyl)-6-(2-chlorophenyl)-1H-pyridin-2-one;

N-[4-[2-(2-chlorophenyl)-6-oxo-1H-pyridin-4-yl]-2-pyridyl]-2-methoxy-acetamide;

N-[4-[2-oxo-6-[2-(trifluoromethyl)-1-piperidyl]-1H-pyridin-4-yl]-2-pyridyl]acetamide;

N-[4-[2-oxo-6-[2-(trifluoromethyl)-1-piperidyl]-1H-pyridin-4-yl]-2-pyridyl]cyclopropanecarboxamide;

N-[4-[2-oxo-6-[3-(trifluoromethyl)morpholin-4-yl]-1H-pyridin-4-yl]-2-pyridyl]acetamide;

methyl N-[4-[2-(2-chlorophenyl)-6-oxo-1H-pyridin-4-yl]-2-pyridyl]carbamate;

methyl N-[4-[2-[1-ethyl-3-(trifluoromethyl)pyrazol-4-yl]-6-oxo-1H-pyridin-4-yl]-2-pyridyl]carbamate;

methyl N-[4-[2-oxo-6-[2-(trifluoromethyl)-3-pyridyl]-1H-pyridin-4-yl]-2-pyridyl]carbamate;

methyl N-[4-[2-(4-methyl-3-pyridyl)-6-oxo-1H-pyridin-4-yl]-2-pyridyl]carbamate;

methyl N-[4-[2-oxo-6-[2-(trifluoromethyl)phenyl]-1H-pyridin-4-yl]-2-pyridyl]carbamate;

N-[4-[2-oxo-6-[2-(trifluoromethyl)phenyl]-1H-pyridin-4-yl]-2-pyridyl]acetamide;

N-[4-[2-(4-methyl-3-pyridyl)-6-oxo-1H-pyridin-4-yl]-2-pyridyl]acetamide;

N-[4-[2-oxo-6-[2-(trifluoromethyl)-3-pyridyl]-1H-pyridin-4-yl]-2-pyridyl]acetamide;

N-[4-[2-[1-ethyl-3-(trifluoromethyl)pyrazol-4-yl]-6-oxo-1H-pyridin-4-yl]-2-pyridyl]acetamide;

methyl N-[4-[2-oxo-6-[3-(trifluoromethyl)morpholin-4-yl]-1H-pyridin-4-yl]-2-pyridyl]carbamate;

methyl N-[4-[2-oxo-6-[2-(trifluoromethyl)-1-piperidyl]-1H-pyridin-4-yl]-2-pyridyl]carbamate;

methyl N-[4-[2-[4-ethylsulfonyl-2-(trifluoromethyl)piperazin-1-yl]-6-oxo-1H-pyridin-4-yl]-2-pyridyl]carbamate;

methyl N-[4-[2-(3-cyclopropylmorpholin-4-yl)-6-oxo-1H-pyridin-4-yl]-2-pyridyl]carbamate;

N-[4-[2-(3-cyclopropylmorpholin-4-yl)-6-oxo-1H-pyridin-4-yl]-2-pyridyl]acetamide;

N-[4-[2-[4-ethylsulfonyl-2-(trifluoromethyl)piperazin-1-yl]-6-oxo-1H-pyridin-4-yl]-2-pyridyl]acetamide;

3-[4-[2-(2-chlorophenyl)-6-oxo-1H-pyridin-4-yl]-2-pyridyl]-1,1-dimethyl-urea; or N-[4-[2-(2-chlorophenyl)-6-oxo-1H-pyridin-4-yl]-2-pyridyl]pyrrolidine-1-carboxamide.

According to one embodiment of this aspect of the invention, said compound is

N-[4-[2-(2-chlorophenyl)-6-oxo-1H-pyridin-4-yl]-2-pyridyl]acetamide;

4-(2-Amino-4-pyridyl)-6-(3-pyridyl)-1H-pyridin-2-one;

4-(2-Amino-4-pyridyl)-6-(2-chlorophenyl)-1H-pyridin-2-one;

N-[4-[2-(2-chlorophenyl)-6-oxo-1H-pyridin-4-yl]-2-pyridyl]-2-methoxy-acetamide;

N-[4-[2-oxo-6-[2-(trifluoromethyl)-1-piperidyl]-1H-pyridin-4-yl]-2-pyridyl]acetamide;

N-[4-[2-oxo-6-[2-(trifluoromethyl)-1-piperidyl]-1H-pyridin-4-yl]-2-pyridyl]cyclopropanecarboxamide;

N-[4-[2-oxo-6-[3-(trifluoromethyl)morpholin-4-yl]-1H-pyridin-4-yl]-2-pyridyl]acetamide;

methyl N-[4-[2-(2-chlorophenyl)-6-oxo-1H-pyridin-4-yl]-2-pyridyl]carbamate;

methyl N-[4-[2-[1-ethyl-3-(trifluoromethyl)pyrazol-4-yl]-6-oxo-1H-pyridin-4-yl]-2-pyridyl]carbamate;

methyl N-[4-[2-oxo-6-[2-(trifluoromethyl)-3-pyridyl]-1H-pyridin-4-yl]-2-pyridyl]carbamate;

methyl N-[4-[2-oxo-6-[2-(trifluoromethyl)phenyl]-1H-pyridin-4-yl]-2-pyridyl]carbamate;

N-[4-[2-oxo-6-[2-(trifluoromethyl)phenyl]-1H-pyridin-4-yl]-2-pyridyl]acetamide;

N-[4-[2-(4-methyl-3-pyridyl)-6-oxo-1H-pyridin-4-yl]-2-pyridyl]acetamide;

N-[4-[2-oxo-6-[2-(trifluoromethyl)-3-pyridyl]-1H-pyridin-4-yl]-2-pyridyl]acetamide;

N-[4-[2-[1-ethyl-3-(trifluoromethyl)pyrazol-4-yl]-6-oxo-1H-pyridin-4-yl]-2-pyridyl]acetamide;

methyl N-[4-[2-oxo-6-[3-(trifluoromethyl)morpholin-4-yl]-1H-pyridin-4-yl]-2-pyridyl]carbamate;

methyl N-[4-[2-oxo-6-[2-(trifluoromethyl)-1-piperidyl]-1H-pyridin-4-yl]-2-pyridyl]carbamate;

N-[4-[2-(3-cyclopropylmorpholin-4-yl)-6-oxo-1H-pyridin-4-yl]-2-pyridyl]acetamide; or N-[4-[2-[4-ethylsulfonyl-2-(trifluoromethyl)piperazin-1-yl]-6-oxo-1H-pyridin-4-yl]-2-pyridyl]acetamide.

In one aspect of the invention, there is provided a compound according to the present invention, for use in the treatment or prophylaxis of a disease.

In one aspect of the invention, there is provided a compound according to the present invention, for use in treating cancer. Typically, said cancer is selected from breast cancer, such as triple negative breast cancer, bladder cancer, liver cancer, cervical cancer, pancreatic cancer, leukemia, lymphoma, renal cancer, colon cancer, glioma, prostate cancer, ovarian cancer, melanoma and lung cancer, as well as hypoxic tumors.

In one aspect of the invention, there is provided a compound according to the present invention, for use in treating type II diabetes.

In one aspect of the invention, there is provided a compound according to the present invention, for use in treating a disease selected from inflammatory diseases, autoimmune diseases, neurodegenerative disorders, cardiovascular disorders and viral infections.

In one aspect of the invention, there is provided use of a compound according to the present invention, in the preparation of a medicament for treating cancer. Typically said cancer is selected from breast cancer, such as triple negative breast cancer, bladder cancer, liver cancer, cervical cancer, pancreatic cancer, leukemia, lymphoma, renal cancer, colon cancer, glioma, prostate cancer, ovarian cancer, melanoma and lung cancer, as well as hypoxic tumors.

In one aspect of the invention, there is provided use of a compound according to the present invention, in the preparation of a medicament for treating type II diabetes.

In one aspect of the invention, there is provided use of a compound according to the present invention, in the preparation of a medicament for treating a disease selected from inflammatory diseases, autoimmune diseases, neurodegenerative disorders, cardiovascular disorders and viral infections.

In one aspect of the invention, there is provided a method of treating cancer, comprising administering a therapeutically effective amount of a compound according to the present invention, to a patient in need thereof. Typically, said cancer is selected from breast cancer, such as triple negative breast cancer, bladder cancer, liver cancer, cervical cancer, pancreatic cancer, leukemia, lymphoma, renal cancer, colon cancer, glioma, prostate cancer, ovarian cancer, melanoma and lung cancer, as well as hypoxic tumors.

In one aspect of the invention, there is provided method of treating hypoxic tumors, comprising administering a therapeutically effective amount of a compound according to the present invention, to a patient in need thereof.

In one aspect of the invention, there is provided a compound according to the present invention, for use in treating cancer, wherein said cancer treatment further comprises radiation therapy.

In one aspect of the invention, there is provided a method of treating cancer, comprising administering a therapeutically effective amount of a compound according to the present invention, to a patient in need thereof, in conjunction with radiation therapy.

The compounds of the present invention may also be employed in cancer treatment in conjunction with radiation therapy and/or surgical intervention. Generally, the use of cytotoxic and/or cytostatic agents in combination with a compound or composition of the present invention will serve to:

(1) yield better efficacy in reducing the growth of a tumor or even eliminate the tumor as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

In one aspect of the invention, there is provided a method of treating type II diabetes, comprising administering a therapeutically effective amount of a compound according to the present invention, to a patient in need thereof.

In one aspect of the invention, there is provided a method of treating a disease selected from inflammatory disease, autoimmune diseases, neurodegenerative disorders, and viral infections, comprising administering a therapeutically effective amount of a compound according to the present invention, to a patient in need thereof.

In one aspect of the invention, there is provided a pharmaceutical composition comprising a compound according to the present invention, and a pharmaceutically acceptable diluent, carrier and/or excipient.

In one aspect of the invention, there is provided a pharmaceutical composition, comprising a therapeutically effective amount of a compound according to according to the present invention and another anticancer agent selected from alkylating agents, antimetabolites, anticancer camptothecin derivatives, plant-derived anticancer agents, antibiotics, enzymes, platinum coordination complexes, tyrosine kinase inhibitors, hormones, hormone antagonists, monoclonal antibodies, interferons, and biological response modifiers.

As used herein, the term "$C_1$-$C_6$alkyl" means both linear and branched chain saturated hydrocarbon groups with 1 to 6 carbon atoms. Examples of $C_1$-$C_6$alkyl groups include methyl, ethyl, n-propyl, isopropyl, n-butyl, iso-butyl, sec-butyl, t-butyl, n-pentyl, 4-methyl-butyl, n-hexyl, 2-ethyl-butyl groups. Among unbranched $C_1$-$C_6$alkyl groups, typical ones are methyl, ethyl, n-propyl, n-butyl, n-pentyl and n-hexyl groups. Among branched alkyl groups, there may be mentioned iso-propyl, iso-butyl, sec-butyl, t-butyl, 4-methyl-butyl and 2-ethyl-butyl groups.

As used herein, the term "$C_1$-$C_3$alkyl" means both linear and branched chain saturated hydrocarbon groups with 1 to 3 carbon atoms. Examples of $C_1$-$C_3$alkyl groups include methyl, ethyl, n-propyl and isopropyl groups.

As used herein, the term "$C_1$-$C_6$alkoxy" means the group O-alkyl, where "$C_1$-$C_6$alkyl" is used as described above. Examples of $C_1$-$C_6$alkoxy groups include, but are not limited to, methoxy, ethoxy, isopropoxy, n-propoxy, n-butoxy, n-hexoxy, 3-methyl-butoxy groups.

As used herein, the term "$C_1$-$C_3$alkoxy" means the group O-alkyl, where "$C_1$-$C_3$alkyl" is used as described above. Examples of $C_1$-$C_3$alkoxy groups include, but are not limited to, methoxy, ethoxy, isopropoxy and n-propoxy.

As used herein, the term "$C_1$-$C_6$haloalkyl" means both linear and branched chain saturated hydrocarbon groups, with 1 to 6 carbon atoms and with 1 to all hydrogens substituted by a halogen of different or same type. Examples of $C_1$-$C_6$haloalkyl groups include methyl substituted with 1 to 3 halogen atoms, ethyl substituted with 1 to 5 halogen atoms, n-propyl or iso-propyl substituted with 1 to 7 halogen atoms, n-butyl or iso-butyl substituted with 1 to 9 halogen atoms, and sec-butyl or t-butyl groups substituted with 1 to 9 halogen atoms.

As used herein, the term "$C_1$-$C_3$haloalkyl" means both linear and branched chain saturated hydrocarbon groups, with 1 to 3 carbon atoms and with 1 to all hydrogens substituted by a halogen of different or same type. Examples of $C_1$-$C_3$haloalkyl groups include methyl substituted with 1 to 3 halogen atoms, ethyl substituted with 1 to 5 halogen atoms, and n-propyl or iso-propyl substituted with 1 to 7 halogen atoms.

As used herein, the term "$C_1$-$C_3$haloalkoxy" means both linear and branched chain saturated alkoxy groups, with 1 to 3 carbon atoms and with 1 to all hydrogen atoms substituted by a halogen atom of different or same type. Examples of $C_1$-$C_3$haloalkoxy groups include methoxy substituted with 1 to 3 halogen atoms, ethoxy substituted with 1 to 5 halogen atoms, and n-propoxy or iso-propoxy substituted with 1 to 7 halogen atoms.

As used herein, the term "$C_1$-$C_3$fluoroalkyl" means both linear and branched chain saturated hydrocarbon groups, with 1 to 3 carbon atoms and with 1 to all hydrogen atoms substituted by a fluorine atom. Examples of $C_1$-$C_3$fluoroalkyl groups include methyl substituted with 1 to 3 fluorine atoms, ethyl substituted with 1 to 5 fluorine atoms, and n-propyl or iso-propyl substituted with 1 to 7 fluorine atoms.

As used herein, the term "$C_1$-$C_3$fluoroalkoxy" means both linear and branched chain saturated alkoxy groups, with 1 to 3 carbon atoms and with 1 to all hydrogen atoms substituted by a fluorine atom. Examples of $C_1$-$C_3$fluoroalkoxy groups include methoxy substituted with 1 to 3 fluorine atoms, ethoxy substituted with 1 to 5 fluorine atoms, and n-propoxy or iso-propoxy substituted with 1 to 7 fluorine atoms.

As used herein, the term "$C_3$-$C_6$cycloalkyl" means a cyclic saturated hydrocarbon group, with 3 to 6 carbon atoms. Examples of $C_3$-$C_6$cycloalkyl groups include cyclopropyl, cyclobutyl, cyclopentyl and cyclohexyl.

As used herein, the term "$C_1$-$C_3$alkoxy$C_1$-$C_3$alkyl" means both a linear and branched chain saturated hydrocarbon group, with 1 to 3 carbon atoms, substituted with an alkoxy group with 1 to 3 carbon atoms. Examples of $C_1$-$C_3$alkoxy$C_1$-$C_3$alkyl groups are drawn below.

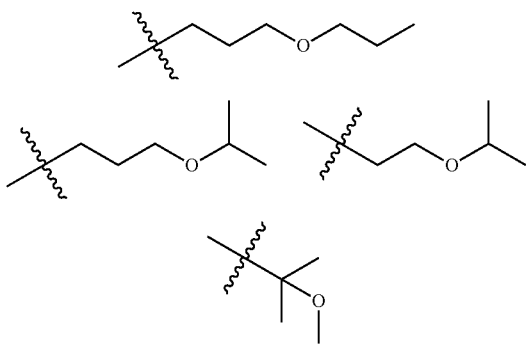

As used herein, the term "$C_1$-$C_3$cyanoalkyl" means both a linear and branched chain cyano (CN) derivative, with one to three carbon atoms including the carbon atom that is part of the cyano group. Examples of $C_1$-$C_3$cyanoalkyl groups are drawn below.

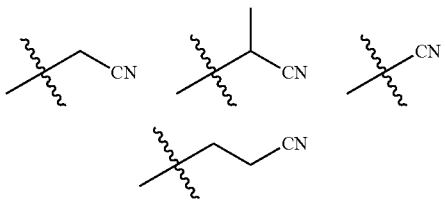

As used herein, the term N—$C_1$-$C_3$alkylamino means an amino substituent carrying one $C_1$-$C_3$alkyl group as defined supra. Examples of N—$C_1$-$C_3$alkylamino are drawn below.

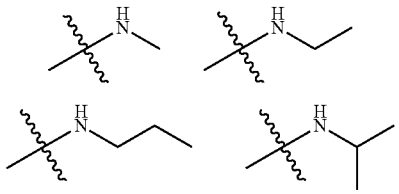

As used herein, the term N,N-di$C_1$-$C_3$alkylamino means an amino substituent carrying two $C_1$-$C_3$alkyl groups as defined supra. Examples of N,N-di$C_1$-$C_3$alkylamino are drawn below.

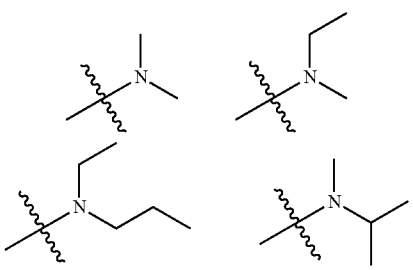

As used herein, the term "halogen" means fluorine, chlorine, bromine or iodine. As used herein, the term "halo" means fluoro, chloro, bromo or iodo.

As used herein, the term "heteroaryl" means a monocyclic aromatic group of carbon atoms wherein from one to three of the carbon atoms is/are replaced by one or more heteroatoms independently selected from nitrogen, oxygen or sulfur. In a bicyclic aryl, one of the rings may be partially saturated.

As used herein, the term "monocyclic heteroaryl" means a monocyclic aromatic group of carbon atoms wherein from one to three of the carbon atoms is/are replaced by one or more heteroatoms independently selected from nitrogen, oxygen or sulfur.

Examples of monocyclic heteroaryl groups include, but are not limited to, furyl, thienyl, pyrrolyl, oxazolyl, thiazolyl, imidazolyl, oxadiazolyl, thiadiazolyl, pyridyl, triazolyl, triazinyl, pyridazyl, isothiazolyl, isoxazolyl, pyrazinyl, pyrazolyl, and pyrimidinyl.

As used herein, the term "heterocyclyl" means a cyclic group of carbon atoms wherein from one to three of the carbon atoms is/are replaced by one or more heteroatoms independently selected from nitrogen, oxygen and sulfur. Examples of heterocyclyl groups include, but are not limited to, tetrahydrofuryl, tetrahydropyranyl, pyrrolidinyl, piperidinyl, piperazinyl, morpholinyl and dioxanyl.

Depending on the substituents present in compounds of the formula (I), the compounds may form salts which are within the scope of the present invention. Salts of compounds of formula (I), which are suitable for use in medicine are those wherein a counterion is pharmaceutically acceptable.

Suitable salts according to the invention include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)alkyl or aryl sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine.

Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucamine, morpholine, thiomorpholine, piperidine, pyrrolidine, a mono, di- or tri lower alkylamine, for example ethyl, tertbutyl, diethyl, diisopropyl, triethyl, tributyl or dimethylpropylamine, or a mono-,di- or trihydroxy lower alkylamine, for example mono-, di- or triethanolamine. Corresponding internal salts may furthermore be formed.

The compounds of the invention may be used in the prophylaxis and/or treatment as such, or in a form of a pharmaceutical composition. While it is possible for the active ingredient to be administered alone, it is also possible for it to be present in a pharmaceutical composition. Accordingly, the invention provides a pharmaceutical composition comprising a compound of formula (I), and a pharmaceutically acceptable diluent, excipient and/or carrier. Pharmaceutical compositions of the invention may take the form of a pharmaceutical composition as described below.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Disintegrators include without limitation starch, methylcellulose, agar, bentonite, xanthan gum and the like. The compounds of formula (I) can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such compositions may be high molecular weight excipients such as celluloses (avicel) or polyethylene glycols (PEG). Such compositions can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

Compositions of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Typical unit dosage compositions are those containing an effective dose, as hereinbefore recited, or an appropriate fraction thereof, of the active ingredient.

It should be understood that in addition to the ingredients particularly mentioned above, the compositions of this invention may include other agents conventional in the art having regard to the type of composition in question, for example those suitable for oral administration may include flavoring agents.

The compositions may be presented in unit dosage form and may be prepared by any of the methods well known in the art of pharmacy. Methods may include the step of bringing the active ingredient into association with the carrier which constitutes one or more accessory ingredients. Compositions may be prepared by uniformly and intimately bringing into association the active ingredient with liquid carriers or finely divided solid carriers or both and then, if necessary, shaping the product into the desired composition.

The compounds of the present invention can also be administered in the form of liposome delivery systems, such as small unilamellar vesicles, large unilamellar vesicles and multilamellar vesicles. Liposomes can be formed from a variety of phospholipids, 1,2-dipalmitoylphosphatidylcholine, phosphatidyl ethanolamine (cephaline), phosphatidylserine, phosphatidylinositol, diphosphatidylglycerol (cardiolipin) or phosphatidylcholine (lecithin).

Compositions for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as polyethylene glycol, ethanol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Compositions for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Compositions for topical administration in the mouth, for example buccally or sublingually, include lozenges comprising the active ingredient in a flavored basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Compounds of formula (I) may be administered as the sole pharmaceutical agent or in combination with one or more additional therapeutic agents where the combination causes no unacceptable adverse effects. This pharmaceutical composition includes administration of a single pharmaceutical dosage composition which contains a compound of formula (I) and one or more additional therapeutic agents, as well as administration of the compound of formula (I) and each additional therapeutic agent in its own separate pharmaceutical dosage composition. For example, a compound of formula (I) and a therapeutic agent may be administered to the patient together in a single oral dosage composition such as a capsule or tablet, or each agent may be administered in compositions with separate dosage.

Where separate dosage compositions are used, the compound of formula (I) and one or more additional therapeutic agents may be administered at essentially the same time (e.g., concurrently) or at separately staggered times (e.g., sequentially).

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions may be provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

Preparation of Compounds

The compounds in the present invention can be prepared as a free base or a pharmaceutically acceptable salt thereof by the process described below. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in *Protective Groups in Organic Synthesis* by T. W. Greene, P. G. M Wutz, 4$^{th}$ Edition, Wiley-Interscience, New York, 2006. It is understood that microwaves can alternatively be used for the heating of reaction mixtures.

Another aspect of the present invention provides a process for preparing a compound of formula (I), or a pharmaceutically acceptable salt thereof, wherein $R^1$, $R^2$, $R^3$ and X are, unless specified otherwise, as defined in herein. Said process comprises of:

(i) Formation of a Corresponding Compound of Formula (I)

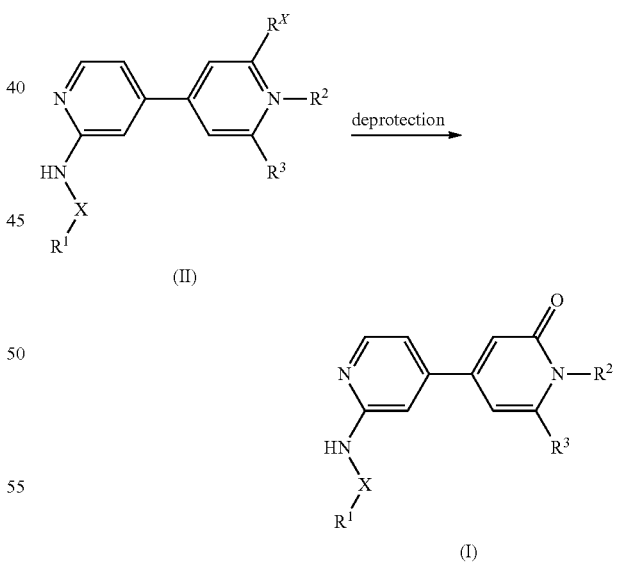

A compound of formula (I) may be obtained (Scheme 1) by starting from, for example, a compound of formula (II), wherein $R^X$ may be F, $OCH_3$, $OC(CH_3)_3$, or $OSiR'R''R'''$ (wherein R', R" and R''' are independently aryl (such as phenyl) or alkyl (such as methyl or tert-butyl)). If $R^X$ is F the conversion into (I) may be carried out by for instance acidic hydrolysis using aqueous HCl. If $R^X$ is $OCH_3$ the conversion into (I) may be carried out by reaction with for instance trimethylsilyl iodide in a suitable solvent such as chloroform or by reaction with HBr in a suitable solvent such as acetic acid or by reaction with BBr$_3$ in a suitable solvent such as dichloromethane. If R$^x$ is OC(CH$_3$)$_3$ the conversion into (I) may be carried out by reaction with for instance trifluoroacetic acid in a suitable solvent such as dichloromethane. If R$^x$ is OSiR'R"R'" the conversion into (I) may be carried out by for instance HCl in a suitable solvent such as methanol or by using tetrabutyl ammonium fluoride in tetrahydrofuran. If enantiomerically pure or enriched compound (II) is used in this reaction, an enantiomerically pure or enantiomerically enriched compound (I) is obtained.

Compounds of formula (II) are commercially available compounds, or are known in the literature, or they are prepared by standard processes known in the art. A compound of formula (I) or (II) may be separated into its enantiomers by standard processes known in the art by for example chromatography on a chiral stationary phase.

General Methods

All solvents used were of analytical grade and commercially available anhydrous solvents were routinely used for reactions. Starting materials were available from commercial sources, or prepared according to literature procedures. Room temperature refers to +20-25° C. Solvent mixture compositions are given as volume percentages or volume ratios. Microwave heating was performed in a Biotage Initiator microwave cavity producing continuous irradiation at 2.45 GHz. It is understood that microwaves may be used for the heating of reaction mixtures.

Straight phase chromatography was manually performed on Merck Silica gel 60 (0.040-0.063 mm), or automatically using an ISCO Combiflash® Companion™ system using SiliaSep™ normal-phase flash columns using the solvent system indicated.

NMR spectra were recorded on a 400 MHz (or higher field) NMR spectrometer fitted with a probe of suitable configuration. Spectra were recorded at ambient temperature unless otherwise stated. Chemical shifts are given in ppm down- and upfield from TMS (0.00 ppm). The following reference signals were used: the residual solvent signal of DMSO-d$_6$ δ2.5, CDCl$_3$ δ 7.26 or Methanol-d$_4$ δ 3.31. Resonance multiplicities are denoted s, d, t, q, m and br for singlet, doublet, triplet, quartet, multiplet and broad, respectively.

High pressure liquid chromatography (HPLC) was performed on a reverse phase column. A linear gradient was applied using for example mobile phase A (aqueous 0.1% NH$_3$ or aqueous 0.1% acetic acid or aqueous 0.1% formic acid) and B (acetonitrile or methanol). Mass spectrometer (MS) analyses were performed in positive ion mode using electrospray ionization (ES+). Preparative chromatography was run on a Gilson-PREP GX271 or GX281 with Trilution lc as software on a reverse phase column. A linear gradient was applied using for example mobile phase A (aqueous 0.1% NH$_3$ or aqueous 0.1% acetic acid or aqueous 0.1% formic acid) and B (acetonitrile or methanol).

Preparative chiral chromatography for separation of enantiomers was run on a Thar SFC using supercritical fluid chromatography on a chiral stationary phase. A linear gradient was applied using mobile phase A (carbon dioxide) and B (acetonitrile or methanol or ethanol or 2-propanol or any mixtures thereof). Additives (such as diethyl amine or isopropyl amine or ammonia or formic acid or TFA) may be used.

Compounds have been named using BIOVIA Draw 16.1.

Abbreviations

Amphos (4-(N,N-Dimethylamino)phenyl)di-tert-butyl phosphine
anh. anhydrous
aq. aqueous
BuLi butyl lithium
DCM dichloromethane
DMAc N,N-dimethyl acetamide
DME 1,2-Dimethoxyethane
DMF N,N-dimethyl formamide
DMSO dimethyl sulfoxide
EtOAc ethyl acetate
EtOH ethanol
h hour(s)
HPLC high pressure (or performance) liquid chromatography
KOtBu potassium tert-butoxide
LCMS liquid chromatography mass spectrometry
MeCN acetonitrile
2-MeTHF 2-methyl tetrahydrofuran
MeOH methanol
min. minute(s)
NMR nuclear magnetic resonance
PEPPSI-iPr [1,3-Bis(2,6-Diisopropylphenyl)imidazol-2-ylidene](3-chloropyridyl)palladium(II) dichloride
Pd(OAc)$_2$ palladium(II) acetate
PdCl$_2$(dppf) [1,1'-Bis(diphenylphosphino)ferrocene]-dichloropalladium(II)
quant. quantitative
rt room temperature
sat. Saturated
S-Phos 2-Dicyclohexylphosphino-2',6'-dimethoxybiphenyl
TFA trifluoroacetic acid
THF tetrahydrofuran Example 1

N-[4-[2-(2-chlorophenyl)-6-oxo-1H-pyridin-4-yl]-2-pyridyl]acetamide

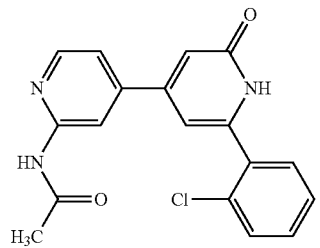 [SMILES: CC(=O)Nc1cc(-c2cc(-c3ccccc3Cl)[nH]c(=O)c2)ccn1]

2,6-Dichloro-4-iodo-pyridine (0.5 g, 1.83 mmol), N-[4-(4,4,5,5-tetramethyl-1,3,2-dioxaborolan-2-yl)-2-pyridyl]acetamide (0.53 g, 2.01 mmol), K$_2$CO$_3$ (0.5 g, 3.65 mmol) and PdCl$_2$(dppf) (0.07 g, 0.09 mmol) were dissolved in DME (3 ml) and water (1 ml) and the mixture was stirred at 80° C. for 1 h. (2-Chlorophenyl)boronic acid (0.29 g, 1.83 mmol), K$_2$CO$_3$ (0.5 g, 3.65 mmol) and PdCl$_2$(dppf) (0.07 g, 0.09 mmol) were added and the mixture was stirred for 4 h at 100° C. The organic layer was separated, filtered and concentrated. The crude material was taken up in toluene (4 ml), KOtBu (0.141 g, 1.26 mmol) was added and the mixture stirred at 100° C. for 30 min. When cooled to rt the mixture was concentrated, dissolved in MeOH/DMF, filtered and purified by preparative HPLC to give the product as a solid (6 mg, 4%). ¹H NMR (500 MHz, METHANOL-d₄) δ ppm 1.92 (s, 1H) 2.22 (s, 3H) 6.75 (s, 1H) 6.87 (s, 1H) 7.43 (dd, 1H) 7.46-7.52 (m, 1H) 7.55 (td, 1H) 7.57-7.67 (m, 2H) 8.39-8.53 (m, 2H). MS ES+ m/z 341 [M+H]⁺.

Example 2

N-[4-(2,6-dichloro-4-pyridyl)-2-pyridyl]acetamide

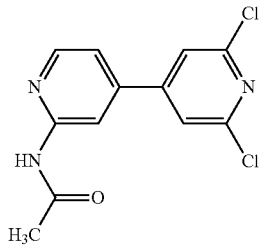 [SMILES: CC(=O)Nc1cc(-c2cc(Cl)nc(Cl)c2)ccn1]

2,6-Dichloro-4-iodo-pyridine (1 g, 3.65 mmol), N-[4-(4,4,5,5-tetramethyl-1,3,2-dioxaborolan-2-yl)-2-pyridyl]acetamide (1.2 g, 4.58 mmol), PdCl₂(PPh₃)₂ (128 mg, 0.18 mmol) and K₂CO₃ (1.51 g, 10.95 mmol) were taken up in 1,4-dioxane:H₂O:EtOH (6:3:1, 15 ml) and nitrogen was bubbled through the mixture for 5 min before being heated to 80° C. for 2 h. When cooled to rt water (10 ml), brine (10 ml) and EtOAc (25 ml) were added, the mixture stirred vigorously for 5 min and the organic layer was separated. The aqueous layer was extracted with EtOAc (3×20 ml) and the combined organics were washed with brine, dried over Na₂SO₄, filtered and concentrated. Recrystallization from MeCN gave the product as a solid (760 mg, 74%). MS ES+ m/z 282 [M+H]⁺.

Example 3

N-[4-(2-benzyloxy-6-chloro-4-pyridyl)-2-pyridyl]acetamide

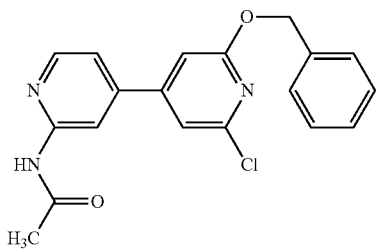 [SMILES: CC(=O)Nc1cc(-c2cc(Cl)nc(OCc3ccccc3)c2)ccn1]

Phenylmethanol (0.7 ml, 6.73 mmol) was added to a suspension of 60% NaH (300 mg, 7.83 mmol) in 2-MeTHF (5 ml) and DMF (5 ml) at 0° C. under a nitrogen atmosphere. The mixture was stirred at rt for 20 min before a solution of N-[4-(2,6-dichloro-4-pyridyl)-2-pyridyl]acetamide (760 mg, 2.69 mmol) in 2-MeTHF (10 ml) and DMF (10 ml) was added and the resulting mixture was stirred at 60° C. for 1.5 h. When cooled to rt water (40 ml) and EtOAc (20 ml) were added and the organic layer separated. The aqueous layer was extracted with EtOAc (2×15 ml) and the combined organics were washed with water (2×15 ml), brine, dried over Na₂SO₄, filtered, concentrated and purified on a silica gel column eluted with 20-75% EtOAc in heptane to give the product as an oil which solidified upon standing (430 mg, 45%). MS ES+ m/z 354 [M+H]⁺.

Example 4

N-[4-[2-benzyloxy-6-(3-pyridyl)-4-pyridyl]-2-pyridyl]acetamide

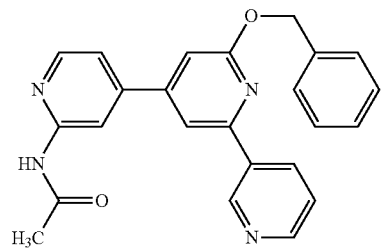

N-[4-(2-benzyloxy-6-chloro-4-pyridyl)-2-pyridyl]acetamide (500 mg, 1.41 mmol), 3-pyridylboronic acid (208 mg, 1.7 mmol), PdCl₂(PPh₃)₂ (50 mg, 0.07 mmol) and K₂CO₃ (585 mg, 4.24 mmol) were taken up in MeCN (15 ml) and water (5 ml). The resulting mixture was stirred at 80° C. overnight. When cooled to rt the mixture was filtered and the organic layer separated. The aqueous layer was extracted with EtOAc (2×10 ml) and the combined organics were dried over Na₂SO₄, filtered and concentrated to give the product as a solid (440 mg, 79%). MS ES+ m/z 397 [M+H]⁺.

Example 5

4-(2-Amino-4-pyridyl)-6-(3-pyridyl)-1H-pyridin-2-one

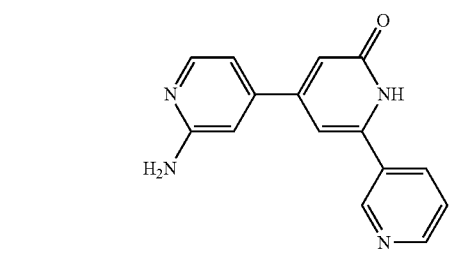 [SMILES: Nc1cc(-c2cc(-c3cccnc3)[nH]c(=O)c2)ccn1]

N-[4-[2-benzyloxy-6-(3-pyridyl)-4-pyridyl]-2-pyridyl]acetamide (440 mg, 1.11 mmol) was taken up in 1,4-dioxane (5 ml) and 2M aq. HCl (4 ml) and the resulting mixture was stirred at 90° C. overnight. When cooled to rt 2M aq. NaOH was added until pH was slightly above 7. The mixture was stirred for 1 h and the resulting precipitate was filtered off, washed with water followed by 1,4-dioxane and dried. The crude product was suspended in MeCN (10 ml), stirred at rt for 1 h, filtered off, washed with MeCN and dried to give the product as a solid (160 mg, 55%). ¹H NMR (500 MHz, DMSO-d₆) δ ppm 11.84 (br. s., 1H), 9.11 (br. s., 1H), 8.66 (d, 1H), 8.30 (d, 1H), 8.07-8.02 (m, 1H), 7.54 (dd, 1H), 7.20 (s, 1H), 7.03 (d, 1H), 6.96 (s, 1H), 6.79-6.63 (m, 3H). MS ES+ m/z 265 [M+H]⁺.

Example 6

6-(2-Chlorophenyl)-4-hydroxy-1H-pyridin-2-one

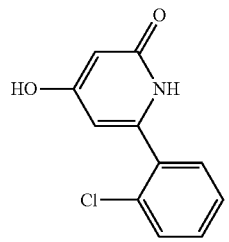 [SMILES: O=c1cc(O)cc(-c2ccccc2Cl)[nH]1]

Ethyl 3-oxobutanoate (6.33 ml, 50 mmol) was added dropwise to a suspension of 60% NaH (1.92 g, 50 mmol) in 2-MeTHF (60 ml) at −78° C. under a nitrogen atmosphere. After 5 min the cooling bath was removed and the mixture was stirred at rt for 20 min. The mixture was cooled back to −78° C. and 1.6 M n-BuLi (31.25 ml, 50 mmol) was added slowly over 20 min. The resulting solution was stirred at −78° C. for 30 min. 2-Chlorobenzonitrile (6.88 g, 50 mmol) was added as a solid in one portion and the reaction mixture was stirred on the thawing cooling bath overnight. The mixture was cooled to 0° C. and MeOH (15 ml) was added slowly. The cooling bath was removed and the mixture stirred at rt for 30 min and then cooled to 0° C. again. The mixture was neutralized by slow addition of conc. HCl and the resulting precipitate was filtered off, washed with EtOH, pentane and dried to give the product as a solid (11.08 g, 87%). MS ES+ m/z 222 [M+H]$^+$.

Example 7

2,4-Dichloro-6-(2-chlorophenyl)pyridine

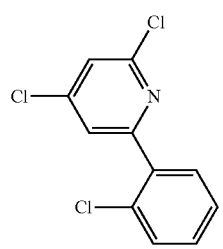 [SMILES: Clc1cc(Cl)nc(-c2ccccc2Cl)c1]

6-(2-Chlorophenyl)-4-hydroxy-1H-pyridin-2-one (5 g, 22.56 mmol) was taken up in POCl$_3$ (40 ml) and N,N-dimethylaniline (5.5 ml, 43.4 mmol) was added slowly. The resulting mixture was refluxed overnight. When cooled to rt the mixture was poured onto ice (600 ml) and stirred at rt for 30 min. The precipitate was filtered off and washed with water. The solid was dissolved in EtOAc (100 ml), dried over Na$_2$SO$_4$, filtered and concentrated to give the product as a solid (7 g, 83%). MS ES+ m/z 258 [M+H]$^+$.

Example 8

4-Chloro-6-(2-chlorophenyl)-1H-pyridin-2-one

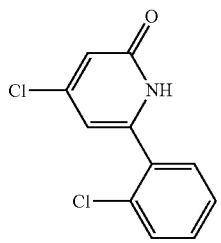 [SMILES: O=c1cc(Cl)cc(-c2ccccc2Cl)[nH]1]

2,4-Dichloro-6-(2-chlorophenyl)pyridine (5.7 g, 22.05 mmol) and KOtBu (6.19 g, 55.12 mmol) were taken up in toluene (75 ml) and the resulting mixture was stirred at 100° C. for 2 h. When cooled to rt, water (40 ml) was added and the organic layer separated. The aqueous layer was made slightly acidic using conc. HCl and extracted with EtOAc (2×40 ml). The combined organics were washed with brine (50 ml), dried over Na$_2$SO$_4$, filtered and concentrated. The resulting residue was taken up in DCM (30 ml) and TFA (5 ml, 67.3 mmol) was added. The reaction mixture was stirred at rt for 1 h, concentrated and the resulting residue was taken up in MeOH (25 ml). 30% NH$_4$OH (20 ml) and water (20 ml) were added and the mixture was stirred at rt overnight. The formed precipitate was filtered off, washed with water, EtOH, pentane and dried to give the product a solid (4.13 g, 78%). MS ES+ m/z 240 [M+H]$^+$.

Example 9

N-(4-chloro-2-pyridyl)-2-methoxy-acetamide

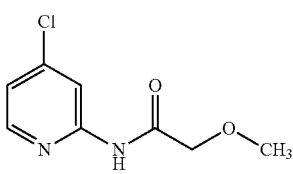

4-Chloropyridin-2-amine (500 mg, 3.89 mmol) and Et$_3$N (1.1 ml, 7.78 mmol) were taken up in DCM (10 ml) at rt and 2-methoxyacetyl chloride (0.53 ml, 5.83 mmol) was added slowly. The resulting mixture was stirred at rt for 15 min. 0.5M aq. HCl (10 ml) was added and the organic layer separated. The aqueous layer was extracted with DCM (5 ml) and the combined organics were dried over Na$_2$SO$_4$, filtered and concentrated to give the product as an oil (750 mg, 96%). MS ES+ m/z 201 [M+H]$^+$.

Example 10

2-Methoxy-N-[4-(4,4,5,5-tetramethyl-1,3,2-dioxaborolan-2-yl)-2-pyridyl]acetamide

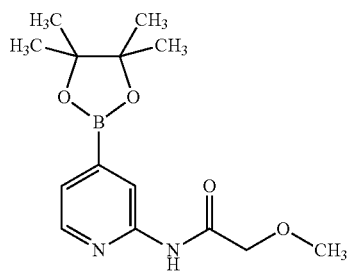

N-(4-chloro-2-pyridyl)-2-methoxy-acetamide (750 mg, 3.74 mmol), 4,4,5,5-tetramethyl-2-(4,4,5,5-tetramethyl-1,3,2-dioxaborolan-2-yl)-1,3,2-dioxaborolane (1.23 g, 4.86 mmol) and KOAc (1.1 g, 11.22 mmol) were taken up in 1,4-dioxane (10 ml) and nitrogen was bubbled through the mixture for 5 min. S-Phos (92 mg, 0.22 mmol) and Pd(OAc)$_2$ (25 mg, 0.11 mmol) were added and the resulting mixture was stirred at 90° C. for 3 h. More S-Phos (92 mg, 0.22 mmol) and Pd(OAc)$_2$ (25 mg, 0.11 mmol) were added and stirring continued for 2 h. When cooled to rt the mixture was filtered through celite and the filter cake washed with EtOAc. The filtrate was diluted with water and the organic layer separated. The aqueous layer was extracted with EtOAc (2×10 ml) and the combined organics were washed with brine, dried over Na$_2$SO$_4$, filtered and concentrated to give the product as an oil, which was used without further purification (1.5 g, quant). MS ES+ m/z 293 [M+H]$^+$.

Example 11 and 12

4-(2-Amino-4-pyridyl)-6-(2-chlorophenyl)-1H-pyridin-2-one and N-[4-[2-(2-chlorophenyl)-6-oxo-1H-pyridin-4-yl]-2-pyridyl]-2-methoxy-acetamide

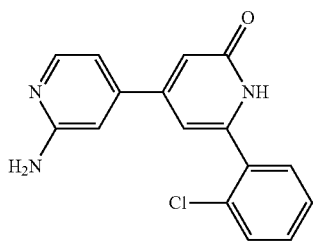 [SMILES: Nc1cc(-c2cc(-c3ccccc3Cl)[nH]c(=O)c2)ccn1]

2-Methoxy-N-[4-(4,4,5,5-tetramethyl-1,3,2-dioxaborolan-2-yl)-2-pyridyl]acetamide (183 mg, 0.62 mmol), 4-chloro-6-(2-chlorophenyl)-1H-pyridin-2-one (100 mg, 0.42 mmol), Pd(PPh$_3$)$_4$ (0.02 g, 0.02 mmol) and K$_2$CO$_3$ (0.17 g, 1.25 mmol) were taken up in 1,4-dioxane:H$_2$O: EtOH (6:3:1, 1.5 ml) and the mixture was heated in a microwave reactor at 150° C. for 15 min. The organic layer was separated and purified by preparative HPLC to give the products. Solid, (12 mg, 10%). $^1$H NMR (500 MHz, DMSO-d$_6$) δ ppm 7.98 (d, 1H), 7.63-7.53 (m, 2H), 7.53-7.40 (m, 3H), 6.80 (dd, 1H), 6.73 (s, 1H), 6.62 (d, 1H), 6.54 (s, 1H), 6.06 (s, 2H). MS ES+ m/z 298 [M+H]$^+$.

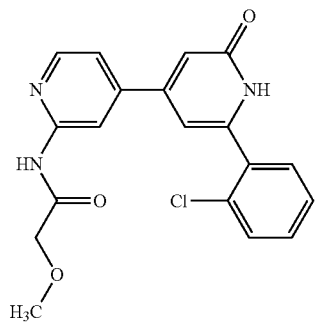 [SMILES: COCC(=O)Nc1cc(-c2cc(-c3ccccc3Cl)[nH]c(=O)c2)ccn1]

Solid, (25 mg, 16%). $^1$H NMR (500 MHz, DMSO-d$_6$) δ ppm 10.23 (br s, 1H), 8.43 (d, 1H), 8.36 (s, 1H), 7.60 (m, 2H), 7.50-7.54 (m, 3H), 6.73 (br s, 1H), 6.54 (s, 1H), 4.07-4.12 (m, 2H), 3.35-3.39 (m, 3H). MS ES+ m/z 370 [M+H]$^+$.

Example 13

4-Benzyloxy-2,6-dichloro-pyridine

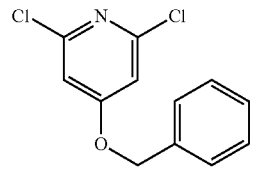 [SMILES: Clc1cc(OCc2ccccc2)cc(Cl)n1]

60% NaH (945 mg, 24.7 mmol) was added portion wise to a solution of 2,4,6-trichloropyridine (4.5 g, 24.7 mmol) in DMF (25 ml) at 0° C. After 20 min phenylmethanol (2.7 g, 24.7 mmol) was added dropwise and the mixture was stirred for 3 h. Water (30 ml) was added and the precipitate was filtered off. The solid was dissolved in EtOAc, dried over MgSO$_4$, filtered and concentrated to give the product as a solid (5 g, 80%). MS ES+ m/z 254 [M+H]$^+$.

Example 14

4-Benzyloxy-2-tert-butoxy-6-chloro-pyridine

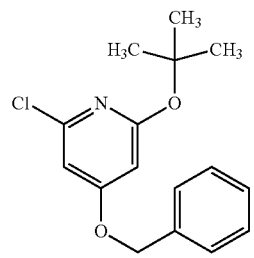 [SMILES: CC(C)(C)Oc1cc(OCc2ccccc2)cc(Cl)n1]

4-Benzyloxy-2,6-dichloro-pyridine (5 g, 19.7 mmol) and KOtBu (2.2 g, 19.7 mmol) were dissolved in 2-MeTHF (25 ml) and the mixture was stirred at 70° C. for 2 h. When cooled to rt the mixture was filtered, concentrated and purified on a silica gel column eluted with 30% EtOAc in heptane to give the product (4 g, 70%). MS ES+ m/z 292 [M+H]$^+$.

Example 15

4-Benzyloxy-2-tert-butoxy-6-[2-(trifluoromethyl)-1-piperidyl]pyridine

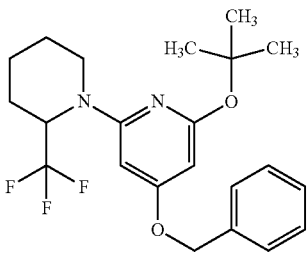 [SMILES: CC(C)(C)Oc1cc(OCc2ccccc2)cc(N2CCCCC2C(F)(F)F)n1]

4-Benzyloxy-2-tert-butoxy-6-chloro-pyridine (4 g, 13.7 mmol), 2-(trifluoromethyl)piperidine (2.3 g, 15.1 mmol), PEPPSI-iPr (146 mg, 1.37 mmol) and KOtBu (3.85 g, 34.3 mmol) were taken up in 1,4-dioxane (30 ml) and the mixture was stirred at 90° C. for 2 h. When cooled to rt water and EtOAc were added and the organic layer separated, filtered, concentrated and purified on silica gel column eluted with 30% EtOAc in heptane to give the product (4.1 g, 73%). MS ES+ m/z 409 [M+H]$^+$.

Example 16

2-tert-Butoxy-6-[2-(trifluoromethyl)-1-piperidyl]pyridin-4-ol

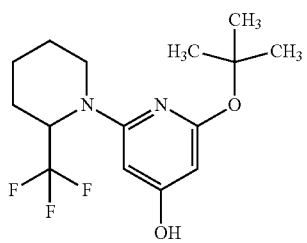 [SMILES: CC(C)(C)Oc1cc(O)cc(N2CCCCC2C(F)(F)F)n1]

A mixture of 4-benzyloxy-2-tert-butoxy-6-[2-(trifluoromethyl)-1-piperidyl]pyridine (3.5 g, 8.57 mmol) and 10% Pd/C (600 mg, 0.56 mmol) in MeOH and EtOAc was hydrogenated (1.5 bar) at rt for 2 h. The mixture was filtered through celite and concentrated to give the product (2.7 g, quant.). MS ES+ m/z 319 [M+H]$^+$.

Example 17

[2-tert-Butoxy-6-[2-(trifluoromethyl)-1-piperidyl]-4-pyridyl]trifluoromethanesulfonate

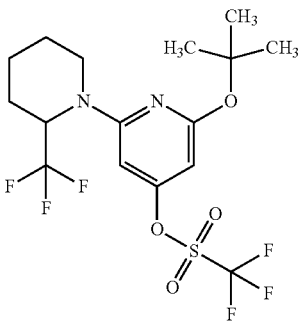 [SMILES: CC(C)(C)Oc1cc(OS(=O)(=O)C(F)(F)F)cc(N2CCCCC2C(F)(F)F)n1]

2-tert-Butoxy-6-[2-(trifluoromethyl)-1-piperidyl]pyridin-4-ol (2.7 g, 8.48 mmol) and Et$_3$N (1.66 ml, 11.9 mmol) was taken up in DCM (20 mL) at 0° C. Trifluoromethylsulfonyl trifluoromethanesulfonate (2.54 ml, 11.9 mmol) was added dropwise over 5 minutes and stirred for 1 h. The mixture was washed with sat. aq. NaHCO$_3$ (2×20 mL), concentrated and purified on silica gel column eluted with 20% EtOAc in heptane to give the product (3.5 g, 92%). MS ES+ m/z 451 [M+H]$^+$.

Example 18

2-tert-Butoxy-4-(4,4,5,5-tetramethyl-1,3,2-dioxaborolan-2-yl)-6-[2-(trifluoromethyl)-1-piperidyl]pyridine

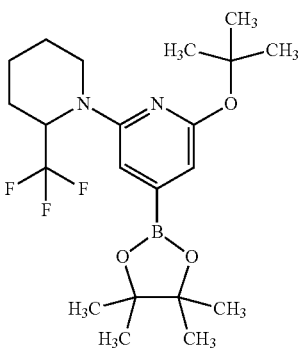 [SMILES: CC(C)(C)Oc1cc(B2OC(C)(C)C(C)(C)O2)cc(N2CCCCC2C(F)(F)F)n1]

4,4,5,5-Tetramethyl-2-(4,4,5,5-tetramethyl-1,3,2-dioxaborolan-2-yl)-1,3,2-dioxaborolane (2.96 g, 11.7 mmol), [2-tert-butoxy-6-[2-(trifluoromethyl)-1-piperidyl]-4-pyridyl] trifluoromethanesulfonate (3.5 g, 7.77 mmol), KOAc (1.14 g, 11.7 mmol) and PdCl$_2$(dppf) (215 mg, 0.29 mmol) were taken up in toluene (10 ml) and stirred at 90° C. for 5 h. When cooled to rt the mixture was concentrated and the residue dissolved in EtOAc, washed with water, concentrated and purified on silica gel column eluted with 0-60% EtOAc in heptane to give the product (2.15 g, 65%). MS ES+ m/z 347 [M+H]$^+$.

Example 19

N-[4-[2-oxo-6-[2-(trifluoromethyl)-1-piperidyl]-1H-pyridin-4-yl]-2-pyridyl]acetamide

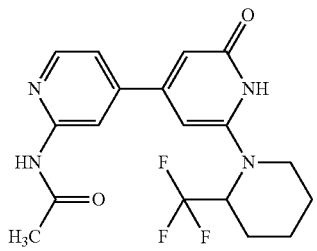 [SMILES: CC(=O)Nc1cc(-c2cc(N3CCCCC3C(F)(F)F)[nH]c(=O)c2)ccn1]

2-tert-Butoxy-4-(4,4,5,5-tetramethyl-1,3,2-dioxaborolan-2-yl)-6-[2-(trifluoromethyl)-1-piperidyl]pyridine (100 mg, 0.23 mmol), N-(4-chloro-2-pyridyl)acetamide (52 mg, 0.3 mmol), $K_2CO_3$ (81 mg, 0.58 mmol) and $PdCl_2(dppf)$ (26 mg, 0.035 mmol) were dissolved in 1,4-dioxane (3 ml) and water (1 ml) and the mixture was stirred at 90° C. for 3 h. Water and EtOAc were added, the organic layer separated and concentrated. The residue was dissolved in DCM and TFA (0.35 ml, 4.67 mmol) was added. The mixture was stirred at rt for 30 min, concentrated and purified by preparative HPLC to give the product as a solid (10 mg, 11%). $^1$H NMR (500 MHz, METHANOL-$d_4$) δ ppm 1.52-1.66 (m, 1H), 1.69-1.77 (m, 2H), 1.76-1.78 (m, 1H), 1.77-1.88 (m, 2H), 2.08 (br d, 1H), 2.20 (s, 3H), 3.22 (br t, 1H), 3.31 (dt, 2H), 3.85 (br d, 1H), 5.12-5.26 (m, 1H), 6.22 (s, 2H), 7.25 (dd, 1H), 8.26-8.36 (m, 2H). MS ES+ m/z 381 [M+H]$^+$.

Example 20

4-[2-tert-Butoxy-6-[2-(trifluoromethyl)-1-piperidyl]-4-pyridyl]pyridin-2-amine

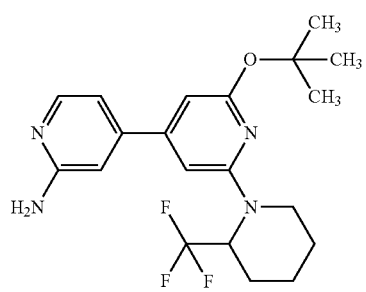 [SMILES: CC(C)(C)Oc1cc(-c2ccnc(N)c2)cc(N2CCCCC2C(F)(F)F)n1]

2-tert-Butoxy-4-(4,4,5,5-tetramethyl-1,3,2-dioxaborolan-2-yl)-6-[2-(trifluoromethyl)-1-piperidyl]pyridine (700 mg, 1.63 mmol), 4-bromopyridin-2-amine (339 mg, 1.96 mmol), $K_2CO_3$ (565 mg, 4.09 mmol) and $PdCl_2(dppf)$ (120 mg, 0.16 mmol) were taken up in dioxane (10 ml) and water (3 ml) and the mixture was stirred at 90° C. for 4 h. When cooled to rt water and EtOAc were added, the organic layer separated, concentrated and purified on a silica gel column eluted with 0-20% MeOH in DCM to give the product as a solid (280 mg, 37%). MS ES+ m/z 395 [M+H]$^+$.

Example 21

N-[4-[2-oxo-6-[2-(trifluoromethyl)-1-piperidyl]-1H-pyridin-4-yl]-2-pyridyl]cyclopropanecarboxamide

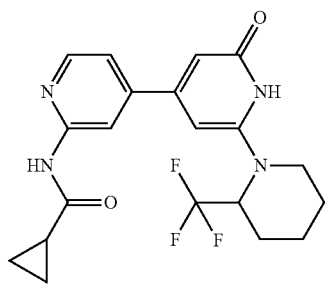 [SMILES: O=C(Nc1cc(-c2cc(N3CCCCC3C(F)(F)F)[nH]c(=O)c2)ccn1)C1CC1]

To a solution of 4-[2-tert-butoxy-6-[2-(trifluoromethyl)-1-piperidyl]-4-pyridyl]pyridin-2-amine (85 mg, 0.22 mmol) in DCM (3 ml) was added cyclopropanecarbonyl chloride (0.022 ml, 0.24 mmol), followed by $Et_3N$ (0.03 ml, 0.22 mmol) and the mixture was stirred at rt for 1 h. The mixture was filtered and TFA (0.08 ml, 1.08 mmol) was slowly added. After 1 h at rt the mixture was concentrated and purified by preparative HPLC to give the product as a solid (8 mg, 9%). $^1$H NMR (500 MHz, DMSO-$d_6$) δ ppm 0.81-0.87 (m, 4H), 1.49 (br d, 1H), 1.68 (br s, 2H), 1.71-1.82 (m, 2H), 1.98-2.07 (m, 2H), 3.04 (br t, 1H), 4.17 (br s, 1H), 5.56 (br s, 1H), 6.19 (s, 1H), 6.50-6.79 (m, 1H), 6.55 (br s, 1H), 7.41 (dd, 1H), 8.34 (s, 1H), 8.39 (dd, 1H), 10.42 (br s, 1H), 10.90 (s, 1H). MS ES+ m/z 407 [M+H]$^+$.

Example 22

4-(4-Benzyloxy-6-tert-butoxy-2-pyridyl)-3-(trifluoromethyl)morpholine

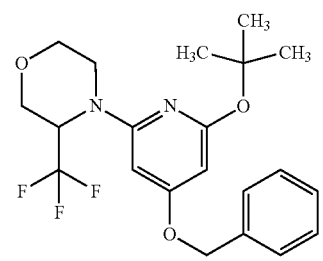

The title compound was prepared as described in Example 15, using 3-(trifluoromethyl)morpholine instead of 2-(trifluoromethyl)piperidine, to give the product as an oil (1 g, 50%). MS ES+ m/z 411 [M+H]$^+$.

Example 23

2-tert-Butoxy-6-[3-(trifluoromethyl)morpholin-4-yl]pyridin-4-ol

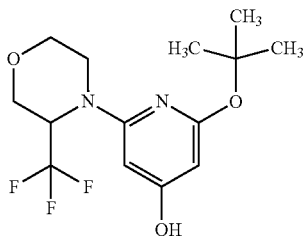 [SMILES: CC(C)(C)Oc1cc(O)cc(N2CCOCC2C(F)(F)F)n1]

The title compound was prepared as described in Example 16, using 4-(4-Benzyloxy-6-tert-butoxy-2-pyridyl)-3-(trifluoromethyl)morpholine instead of 4-benzyloxy-2-tert-butoxy-6-[2-(trifluoromethyl)-1-piperidyl]pyridineto give the product (780 mg, 99%). MS ES+ m/z 321 [M+H]+.

Example 24

[2-tert-Butoxy-6-[3-(trifluoromethyl)morpholin-4-yl]-4-pyridyl]trifluoromethanesulfonate

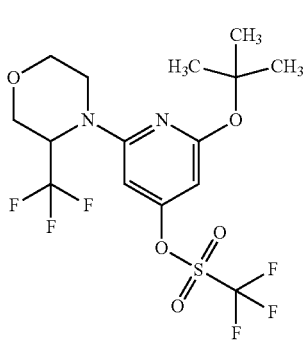 [SMILES: CC(C)(C)Oc1cc(OS(=O)(=O)C(F)(F)F)cc(N2CCOCC2C(F)(F)F)n1]

The title compound was prepared as described in Example 17, using 2-tert-butoxy-6-[3-(trifluoromethyl)morpholin-4-yl]pyridin-4-ol instead of 2-tert-butoxy-6-[2-(trifluoromethyl)-1-piperidyl]pyridin-4-ol to give the product as an oil (800 mg, 81%). MS ES+ m/z 453 [M+H]+.

Example 25

4-[6-tert-Butoxy-4-(4,4,5,5-tetramethyl-1,3,2-dioxaborolan-2-yl)-2-pyridyl]-3-(trifluoromethyl)morpholine

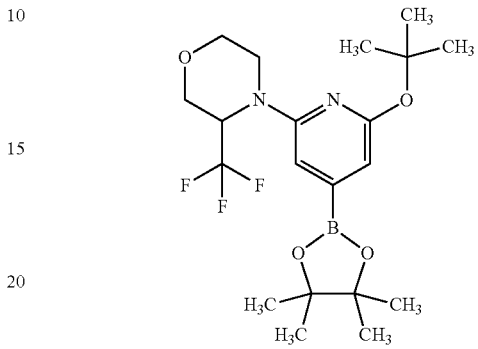

The title compound was prepared as described in Example 18, using [2-tert-butoxy-6-[3-(trifluoromethyl)morpholin-4-yl]-4-pyridyl] trifluoromethanesulfonate instead of [2-tert-butoxy-6-[2-(trifluoromethyl)-1-piperidyl]-4-pyridyl] trifluoromethanesulfonate, to give the product (270 mg, 33%). MS ES+ m/z 431 [M+H]+.

Example 26

N-[4-[2-oxo-6-[3-(trifluoromethyl)morpholin-4-yl]-1H-pyridin-4-yl]-2-pyridyl]acetamide

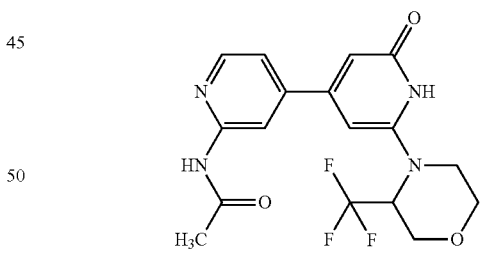

The title compound was prepared as described in Example 19, using 4-[6-tert-butoxy-4-(4,4,5,5-tetramethyl-1,3,2-dioxaborolan-2-yl)-2-pyridyl]-3-(trifluoromethyl)morpholine instead of 2-tert-butoxy-4-(4,4,5,5-tetramethyl-1,3,2-dioxaborolan-2-yl)-6-[2-(trifluoromethyl)-1-piperidyl]pyridine, to give the product as a solid (20 mg, 25%). 1H NMR (500 MHz, DMSO-d6) δ ppm 2.13 (s, 3H), 3.25-3.31 (m, 1H), 3.51-3.57 (m, 1H), 3.72-3.78 (m, 1H), 3.94-4.04 (m, 2H), 4.19 (d, 1H), 5.31 (br d, 1H), 6.25 (s, 1H), 6.56 (br s, 1H), 7.41 (d, 1H), 8.34 (s, 1H), 8.39 (dd, 1H), 10.55 (br s, 1H), 10.60 (s, 1H). MS ES+ m/z 383 [M+H]+.

Example 27

N-[4-(2-tert-butoxy-6-chloro-4-pyridyl)-2-pyridyl]acetamide

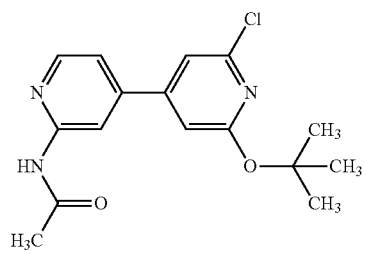 [SMILES: CC(=O)Nc1cc(-c2cc(Cl)nc(OC(C)(C)C)c2)ccn1]

A mixture of N-[4-(4,4,5,5-tetramethyl-1,3,2-dioxaborolan-2-yl)-2-pyridyl]acetamide (3 g, 9.62 mmol), 2-tert-butoxy-6-chloro-4-iodo-pyridine (*Bioorganic & Medicinal Chemistry Letters* (2012), 22, (5), 1940-1943, 2.52 g, 9.62 mmol) and $Na_2CO_3$ (3.05 g, 28.86 mmol) in 1,4-dioxane (20 ml) and water (4 ml) was degassed with nitrogen for 20 min. $PdCl_2(dppf)$ (351 mg, 0.48 mmol) was added and the resulting mixture was heated and stirred at 110° C. overnight. When cooled to rt EtOAc was added, the mixture filtered through celite, concentrated and purified by preparative HPLC to give the product as a solid (1.58 g, 22%). MS ES+ m/z 320 $[M+H]^+$.

Example 28

1-Ethylsulfonyl-3-(trifluoromethyl)piperazine

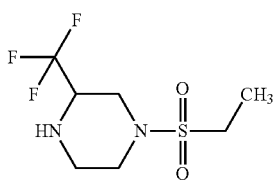

Ethanesulfonyl chloride (1.18 ml, 12.5 mmol) was added slowly to a solution of 2-(trifluoromethyl)-piperazine (1.93 g, 12.5 mmol) and TEA (2.09 ml, 15 mmol) in DCM (40 ml) at 0° C. and the resulting mixture was stirred at rt overnight. DCM (50 ml) and water (60 ml) were added, the organic layer separated, and the aqueous layer was extracted with DCM (2×50 ml). The combined organics were washed twice with brine, dried over $Na_2SO_4$, filtered and concentrated to give the product as a solid (3 g, 98%). $^1$H NMR (500 MHz, DMSO-$d_6$) δ ppm 1.21 (t, 3H), 2.64-2.70 (m, 1H), 2.86-3.03 (m, 4H), 3.07-3.16 (m, 2H), 3.36-3.38 (m, 1H), 3.41-3.49 (m, 1H), 3.53 (dd, 1H).

Example 29

N-[4-[2-tert-butoxy-6-[4-ethylsulfonyl-2-(trifluoromethyl)piperazin-1-yl]-4-pyridyl]-2-pyridyl]acetamide

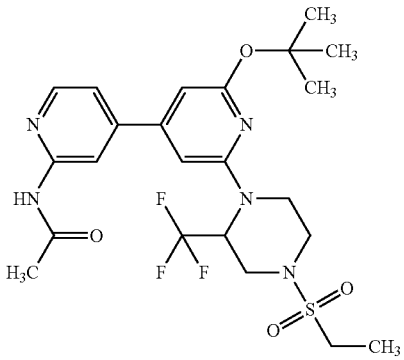 [SMILES: CCS(=O)(=O)N1CCN(c2cc(-c3ccnc(NC(C)=O)c3)cc(OC(C)(C)C)n2)C(C(F)(F)F)C1]

A mixture of N-[4-(2-tert-butoxy-6-chloro-4-pyridyl)-2-pyridyl]acetamide (96 mg, 0.3 mmol), 1-ethylsulfonyl-3-(trifluoromethyl)piperazine (81 mg, 0.33 mmol), $Cs_2CO_3$ (98 mg, 0.3 mmol), Xantphos (174 mg, 0.3 mmol) and $Pd(OAc)_2$ (67 mg, 0.3 mmol) in 1,4-dioxane (2 ml) was stirred under argon in a sealed tube 100° C. for 6 h. When cooled to rt water was added and the mixture was extracted with EtOAc. The combined organics were washed with brine, dried over $Na_2SO_4$, filtered, concentrated and purified on a silica gel column eluted with 0-5% MeOH in DCM to give the product as a solid (110 mg, 55%). MS ES+ m/z 530 $[M+H]^+$.

Example 30

N-[4-[2-[4-ethylsulfonyl-2-(trifluoromethyl)piperazin-1-yl]-6-oxo-1H-pyridin-4-yl]-2-pyridyl]acetamide

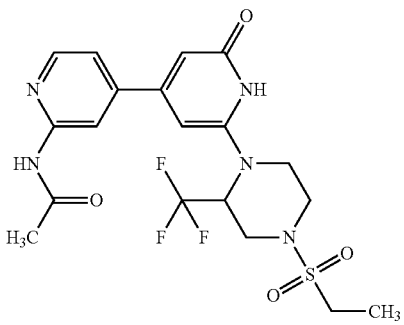 [SMILES: CCS(=O)(=O)N1CCN(c2cc(-c3ccnc(NC(C)=O)c3)cc(=O)[nH]2)C(C(F)(F)F)C1]

TFA (0.91 ml, 12.2 mmol) was added to a solution of N-[4-[2-tert-butoxy-6-[4-ethylsulfonyl-2-(trifluoromethyl) piperazin-1-yl]-4-pyridyl]-2-pyridyl]acetamide (108 mg, 0.2 mmol) in DCM (8 ml) at 0° C. and the resulting mixture was stirred at 0° C. for 1 h. The mixture was concentrated and purified by preparative HPLC to give the product as a solid (27 mg, 28%). $^1$H NMR (500 MHz, DMSO-$d_6$) δ ppm 1.23 (t, 3H), 2.09-2.16 (m, 3H), 2.94-3.05 (m, 1H), 3.10-3.32 (m, 3H), 3.66 (br d, 1H), 3.94 (br d, 1H), 4.11 (q, 1H), 4.34 (br d, 1H), 5.65 (br s, 1H), 6.27 (s, 1H), 6.65 (s, 1H), 7.42 (dd, 1H), 8.34 (s, 1H), 8.40 (d, 1H), 10.63 (br s, 1H), 10.67 (s, 1H). MS ES+ m/z 474 [M+H]+.

Example 31

N-[4-[2-tert-butoxy-6-(3-cyclopropylmorpholin-4-yl)-4-pyridyl]-2-pyridyl]acetamide

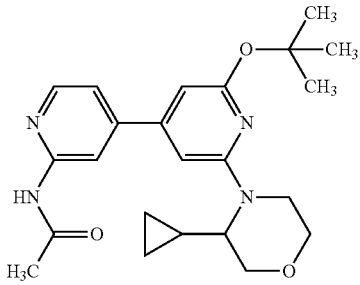 [SMILES: CC(=O)Nc1cc(-c2cc(OC(C)(C)C)nc(N3CCOCC3C3CC3)c2)ccn1]

The title compound was prepared as described in Example 29, using 3-cyclopropylmorpholine, to give the product as a solid (44 mg, 29%). MS ES+m/z 411 [M+H]+.

Example 32

N-[4-[2-(3-cyclopropylmorpholin-4-yl)-6-oxo-1H-pyridin-4-yl]-2-pyridyl]acetamide

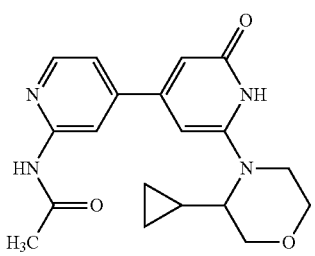 [SMILES: CC(=O)Nc1cc(-c2cc(N3CCOCC3C3CC3)[nH]c(=O)c2)ccn1]

The title compound was prepared as described in Example 30, to give the product as a solid (8 mg, 21%). 1H NMR (500 MHz, DMSO-d6) δ ppm 0.29-0.48 (m, 4H), 1.37-1.50 (m, 1H), 2.11-2.17 (m, 3H), 3.34-3.40 (m, 1H), 3.48 (td, 1H), 3.57 (dd, 1H), 3.76-3.96 (m, 4H), 6.07 (s, 1H), 6.32 (br s, 1H), 7.37 (d, 1H), 8.32 (s, 1H), 8.34-8.40 (m, 1H), 10.02-10.44 (m, 1H), 10.58 (br s, 1H). MS ES+ m/z 355 [M+H]+.

Example 33

N-[4-[2-tert-butoxy-6-[2-(trifluoromethyl)phenyl]-4-pyridyl]-2-pyridyl]acetamide

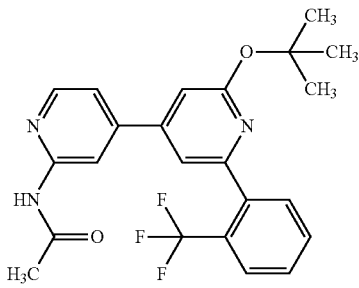 [SMILES: CC(=O)Nc1cc(-c2cc(OC(C)(C)C)nc(-c3ccccc3C(F)(F)F)c2)ccn1]

N-[4-(2-tert-butoxy-6-chloro-4-pyridyl)-2-pyridyl]acetamide (96 mg, 0.3 mmol), [2-(trifluoromethyl)phenyl]boronic acid (86 mg, 0.45 mmol), K2CO3 (83 mg, 0.6 mmol) and PdCl2(Amphos) (11 mg, 0.02 mmol) were taken up in 1,4-dioxane (1.5 ml) and water (0.5 ml) and the resulting mixture was stirred at 100° C. for 1 h. When cooled to rt, brine was added and the mixture extracted with EtOAc. The combined organics were washed with brine, dried over Na2SO4, filtered, concentrated and purified on a silica gel column eluted with 0-100% EtOAc in isohexane to give the product as a solid (105 mg, 82%). MS ES+ m/z 430 [M+H]+.

Example 34

N-[4-[2-oxo-6-[2-(trifluoromethyl)phenyl]-1H-pyridin-4-yl]-2-pyridyl]acetamide

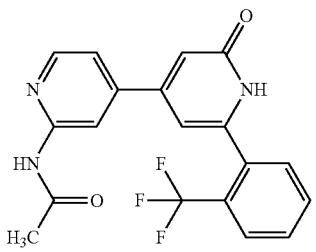 [SMILES: CC(=O)Nc1cc(-c2cc(-c3ccccc3C(F)(F)F)[nH]c(=O)c2)ccn1]

The title compound was prepared as described in Example 30, to give the product as a solid (42 mg, 47%). 1H NMR (500 MHz, DMSO-d6) δ ppm 2.12 (s, 3H), 6.33-6.61 (m, 1H), 6.74 (br s, 1H), 7.43 (dd, 1H), 7.66 (d, 1H), 7.71-7.83 (m, 2H), 7.89 (d, 1H), 8.35-8.43 (m, 2H), 10.64 (s, 1H), 11.86-12.38 (m, 1H). MS ES+ m/z 374 [M+H]+.

Example 35

N-[4-[2-tert-butoxy-6-[2-(trifluoromethyl)-3-pyridyl]-4-pyridyl]-2-pyridyl]acetamide

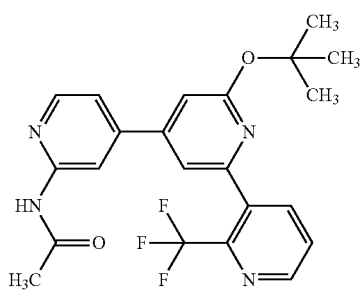 [SMILES: CC(=O)Nc1cc(-c2cc(OC(C)(C)C)nc(-c3cccnc3C(F)(F)F)c2)ccn1]

N-[4-(3-tert-butoxy-5-chloro-phenyl)-2-pyridyl]acetamide (128 mg, 0.4 mmol), [2-(trifluoromethyl)-3-pyridyl]boronic acid (84 mg, 0.44 mmol), K$_2$CO$_3$ (111 mg, 0.8 mmol) and PdCl$_2$(Amphos) (14 mg, 0.02 mmol) were taken up in 1,4-dioxane (2.5 ml) and water (0.5 ml) and the resulting mixture was stirred at 90° C. for 4 h. More [2-(trifluoromethyl)-3-pyridyl]boronic acid (84 mg, 0.44 mmol) was added followed by PdCl$_2$(dppf) (29 mg, 0.04 mmol) and the mixture was stirred at 90° C. overnight. When cooled to rt, water was added and the mixture extracted with EtOAc. The combined organics were washed with brine, dried over Na$_2$SO$_4$, filtered, concentrated and purified on a silica gel column eluted with 0-5% MeOH in DCM to give the product as a solid (70 mg, 41%). MS ES+ m/z 431 [M+H]$^+$.

Example 36

N-[4-[2-oxo-6-[2-(trifluoromethyl)-3-pyridyl]-1H-pyridin-4-yl]-2-pyridyl]acetamide

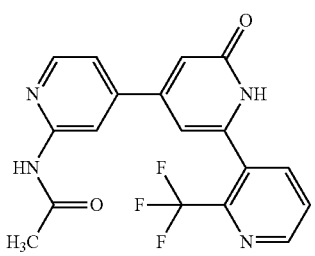 [SMILES: CC(=O)Nc1cc(-c2cc(-c3cccnc3C(F)(F)F)[nH]c(=O)c2)ccn1]

The title compound was prepared as described in Example 30, to give the product as a solid (30 mg, 54%). $^1$H NMR (500 MHz, DMSO-d$_6$) δ ppm 2.08-2.16 (m, 3H), 6.43-6.93 (m, 1H), 6.81 (br s, 1H), 7.44 (dd, 1H), 7.86 (dd, 1H), 8.18 (d, 1H), 8.36-8.44 (m, 2H), 8.87 (s, 1H), 10.65 (s, 1H), 11.75-12.42 (m, 1H). MS ES+ m/z 375 [M+H]$^+$.

Example 37

N-[4-[2-tert-butoxy-6-(2-methyl-3-pyridyl)-4-pyridyl]-2-pyridyl]acetamide

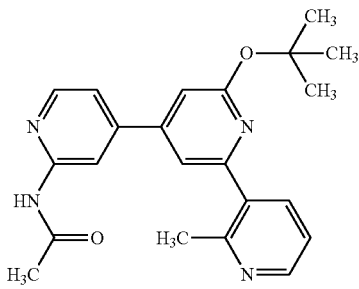 [SMILES: CC(=O)Nc1cc(-c2cc(OC(C)(C)C)nc(-c3cccnc3C)c2)ccn1]

The title compound was prepared as described in Example 33, using (2-methyl-3-pyridyl)boronic acid, to give the product as a solid (110 mg, 93%). MS ES+ m/z 377 [M+H]$^+$.

Example 38

N-[4-[2-(2-methyl-3-pyridyl)-6-oxo-1H-pyridin-4-yl]-2-pyridyl]acetamide

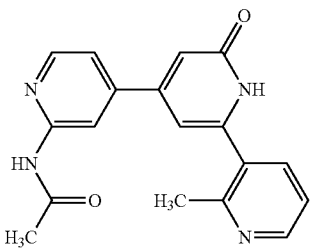 [SMILES: CC(=O)Nc1cc(-c2cc(-c3cccnc3C)[nH]c(=O)c2)ccn1]

The title compound was prepared as described in Example 30, to give the product as a solid (32 mg, 36%). $^1$H NMR (500 MHz, DMSO-d$_6$) δ ppm 2.08-2.14 (m, 3H), 2.47 (s, 3H), 6.58 (br s, 1H), 6.69 (s, 1H), 7.36 (dd, 1H), 7.47 (dd, 1H), 7.81 (dd, 1H), 8.35-8.44 (m, 2H), 8.56 (dd, 1H), 10.67 (s, 1H), 12.03 (br s, 1H). MS ES+ m/z 321 [M+H]$^+$.

Example 39

N-[4-[2-tert-butoxy-6-(4-methyl-3-pyridyl)-4-pyridyl]-2-pyridyl]acetamide

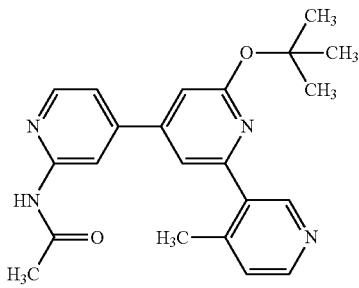 [SMILES: CC(=O)Nc1cc(-c2cc(OC(C)(C)C)nc(-c3cnccc3C)c2)ccn1]

The title compound was prepared as described in Example 33, using (4-methyl-3-pyridyl)boronic acid, to give the product as a solid (110 mg, 78%). MS ES+ m/z 377 [M+H]+.

Example 40

N-[4-[2-(4-methyl-3-pyridyl)-6-oxo-1H-pyridin-4-yl]-2-pyridyl]acetamide

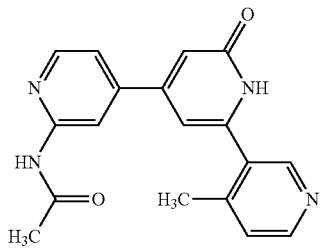 [SMILES: CC(=O)Nc1cc(-c2cc(-c3cnccc3C)[nH]c(=O)c2)ccn1]

The title compound was prepared as described in Example 30, to give the product as a solid (40 mg, 45%). $^1$H NMR (500 MHz, DMSO-$d_6$) δ ppm 2.12 (s, 3H), 2.36 (s, 3H), 6.60 (br s, 1H), 6.70 (s, 1H), 7.39 (d, 1H), 7.48 (dd, 1H), 8.36-8.44 (m, 2H), 8.53 (d, 1H), 8.55 (s, 1H), 10.67 (s, 1H), 12.02 (br s, 1H). MS ES+ m/z 321 [M+H]+.

Example 41

N-[4-[2-tert-butoxy-6-[4-(trifluoromethyl)-3-thienyl]-4-pyridyl]-2-pyridyl]acetamide

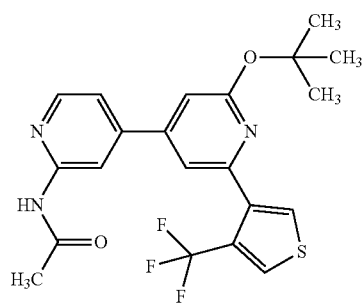 [SMILES: CC(=O)Nc1cc(-c2cc(OC(C)(C)C)nc(-c3cscc3C(F)(F)F)c2)ccn1]

The title compound was prepared as described in Example 33, using [4-(trifluoromethyl)-3-thienyl]boronic acid, to give the product as a solid (120 mg, 64%). MS ES+ m/z 436 [M+H]+.

Example 42

N-[4-[2-oxo-6-[4-(trifluoromethyl)-3-thienyl]-1H-pyridin-4-yl]-2-pyridyl]acetamide

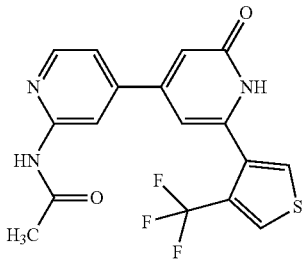 [SMILES: CC(=O)Nc1cc(-c2cc(-c3cscc3C(F)(F)F)[nH]c(=O)c2)ccn1]

The title compound was prepared as described in Example 30, to give the product as a solid (27 mg, 40%). $^1$H NMR (500 MHz, DMSO-$d_6$) δ ppm 2.12 (s, 3H), 6.65 (br s, 1H), 6.75 (br s, 1H), 7.43 (dd, 1H), 8.10 (d, 1H), 8.35-8.46 (m, 3H), 10.67 (s, 1H), 11.90 (br s, 1H). MS ES+ m/z 380 [M+H]+.

Example 43

N-[4-[2-tert-butoxy-6-[1-ethyl-3-(trifluoromethyl)pyrazol-4-yl]-4-pyridyl]-2-pyridyl]acetamide

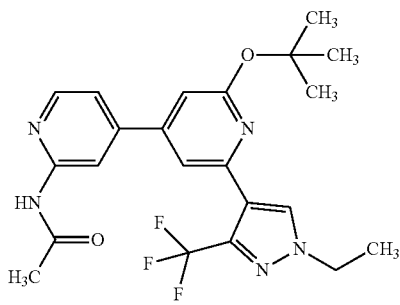 [SMILES: CCn1cc(-c2cc(-c3ccnc(NC(C)=O)c3)cc(OC(C)(C)C)n2)c(C(F)(F)F)n1]

The title compound was prepared as described in Example 33, using 1-ethyl-3-(trifluoromethyl)pyrazol-4-yl]boronic acid, to give the product as a solid (62 mg, 46%). MS ES+ m/z 448 [M+H]+.

Example 44

N-[4-[2-[1-ethyl-3-(trifluoromethyl)pyrazol-4-yl]-6-oxo-1H-pyridin-4-yl]-2-pyridyl]acetamide

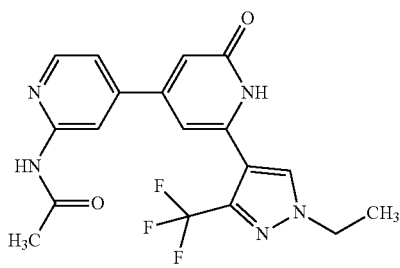 [SMILES: CCn1cc(-c2cc(-c3ccnc(NC(C)=O)c3)cc(=O)[nH]2)c(C(F)(F)F)n1]

The title compound was prepared as described in Example 30, to give the product as a solid (18 mg, 34%). ¹H NMR (500 MHz, DMSO-d₆) δ ppm 1.45 (t, 3H), 2.13 (s, 3H), 4.28 (q, 2H), 6.70 (br s, 2H), 7.40 (dd, 1H), 8.37-8.45 (m, 3H), 10.65 (s, 1H), 11.32-12.66 (m, 1H). MS ES+ m/z 392 [M+H]⁺.

Example 45

Methyl N-[4-[2-oxo-6-[3-(trifluoromethyl)morpholin-4-yl]-1H-pyridin-4-yl]-2-pyridyl]carbamate

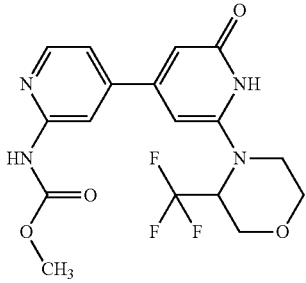

The title compound was prepared as described in Example 19, using 4-[6-tert-butoxy-4-(4,4,5,5-tetramethyl-1,3,2-dioxaborolan-2-yl)-2-pyridyl]-3-(trifluoromethyl)morpholine and methyl N-(4-chloro-2-pyridyl)carbamate, to give the product as a solid (35 mg, 36%). ¹H NMR (500 MHz, DMSO-d₆) δ ppm 3.24-3.37 (m, 1H), 3.54 (td, 1H), 3.71 (s, 3H), 3.72-3.79 (m, 1H), 3.91-4.06 (m, 2H), 4.20 (d, 1H), 5.31 (br d, 1H), 6.26 (s, 1H), 6.57 (br s, 1H), 7.37 (dd, 1H), 8.08-8.10 (m, 1H), 8.35 (dd, 1H), 10.30 (s, 1H), 10.56 (br s, 1H). MS ES+ m/z 399 [M+H]⁺.

Example 46

Methyl N-[4-(2-tert-butoxy-6-chloro-4-pyridyl)-2-pyridyl]carbamate

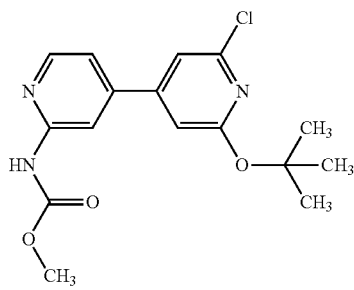 [SMILES: COC(=O)Nc1cc(-c2cc(Cl)nc(OC(C)(C)C)c2)ccn1]

The title compound was prepared as described in Example 27, using methyl N-[4-(4,4,5,5-tetramethyl-1,3,2-dioxaborolan-2-yl)-2-pyridyl]carbamate, to give the product as a solid (940 mg, 26%). MS ES+ m/z 336 [M+H]⁺.

Example 47

Methyl N-[4-[2-tert-butoxy-6-[2-(trifluoromethyl)phenyl]-4-pyridyl]-2-pyridyl]carbamate

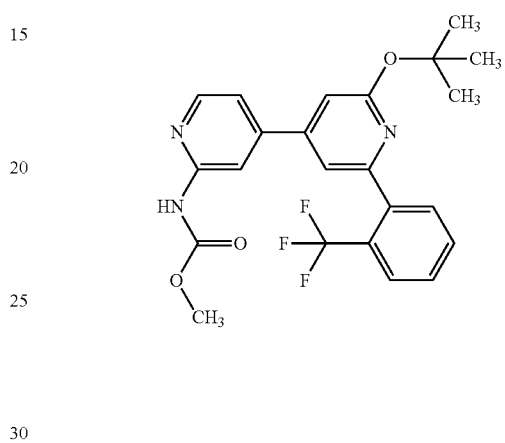

The title compound was prepared as described in Example 33, using methyl N-[4-(2-tert-butoxy-6-chloro-4-pyridyl)-2-pyridyl]carbamate, to give the product as a solid (126 mg, 94%). MS ES+ m/z 446 [M+H]⁺.

Example 48

Methyl N-[4-[2-oxo-6-[2-(trifluoromethyl)phenyl]-1H-pyridin-4-yl]-2-pyridyl]carbamate

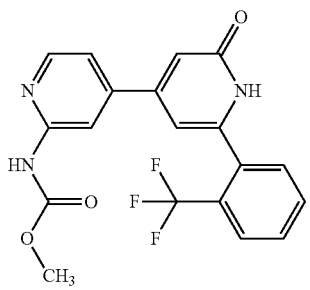

The title compound was prepared as described in Example 30, to give the product as a solid (40 mg, 37%). ¹H NMR (500 MHz, DMSO-d₆) δ ppm 3.62-3.79 (m, 3H), 6.53 (s, 1H), 6.75 (br s, 1H), 7.39 (dd, 1H), 7.66 (d, 1H), 7.71-7.82 (m, 2H), 7.89 (d, 1H), 8.09-8.14 (m, 1H), 8.35-8.39 (m, 1H), 10.36 (s, 1H), 12.01 (br s, 1H). MS ES+ m/z 390 [M+H]⁺.

Example 49

Methyl N-[4-[2-tert-butoxy-6-(2-chlorophenyl)-4-pyridyl]-2-pyridyl]carbamate

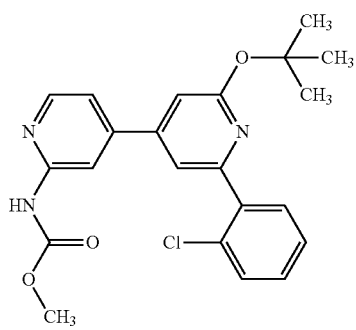 [SMILES: COC(=O)Nc1cc(-c2cc(OC(C)(C)C)nc(-c3ccccc3Cl)c2)ccn1]

The title compound was prepared as described in Example 20, using methyl N-[4-(2-tert-butoxy-6-chloro-4-pyridyl)-2-pyridyl]carbamate and (2-chlorophenyl)boronic acid, to give the product as a solid (82 mg, 66%). MS ES+ m/z 412 [M+H]+.

Example 50

Methyl N-[4-[2-(2-chlorophenyl)-6-oxo-1H-pyridin-4-yl]-2-pyridyl]carbamate

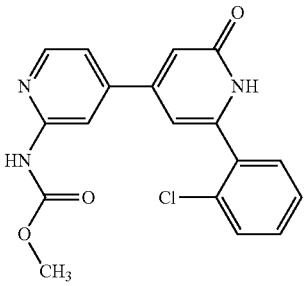 [SMILES: COC(=O)Nc1cc(-c2cc(-c3ccccc3Cl)[nH]c(=O)c2)ccn1]

The title compound was prepared as described in Example 30, to give the product as a solid (8 mg, 12%). $^1$H NMR (500 MHz, DMSO-$d_6$) δ ppm 3.67-3.73 (m, 3H), 6.60 (br s, 1H), 6.72 (br s, 1H), 7.39-7.55 (m, 3H), 7.58-7.63 (m, 2H), 8.12 (s, 1H), 8.37 (d, 1H), 10.36 (s, 1H), 12.00 (br s, 1H). MS ES+ m/z 356 [M+H]+.

Example 51

Methyl N-[4-[2-tert-butoxy-6-[2-(trifluoromethyl)-3-pyridyl]-4-pyridyl]-2-pyridyl]carbamate

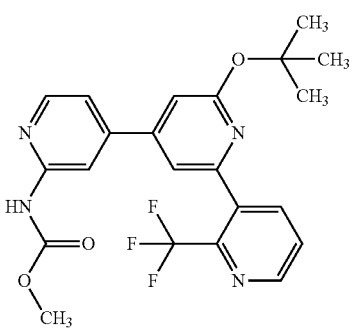 [SMILES: COC(=O)Nc1cc(-c2cc(OC(C)(C)C)nc(-c3cccnc3C(F)(F)F)c2)ccn1]

The title compound was prepared as described in Example 20, using methyl N-[4-(2-tert-butoxy-6-chloro-4-pyridyl)-2-pyridyl]carbamate and [2-(trifluoromethyl)-3-pyridyl]boronic acid, to give the product as a solid (57 mg, 43%). MS ES+ m/z 447 [M+H]+.

Example 52

Methyl N-[4-[2-oxo-6-[2-(trifluoromethyl)-3-pyridyl]-1H-pyridin-4-yl]-2-pyridyl]carbamate

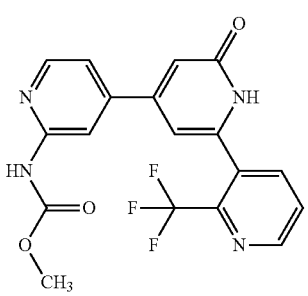 [SMILES: COC(=O)Nc1cc(-c2cc(-c3cccnc3C(F)(F)F)[nH]c(=O)c2)ccn1]

The title compound was prepared as described in Example 30, to give the product as a solid (18 mg, 40%). $^1$H NMR (500 MHz, DMSO-$d_6$) δ ppm 3.71 (s, 3H), 6.41-6.77 (m, 1H), 6.82 (br s, 1H), 7.39-7.43 (m, 1H), 7.86 (dd, 1H), 8.13 (s, 1H), 8.18 (d, 1H), 8.36-8.40 (m, 1H), 8.88 (d, 1H), 10.37 (s, 1H), 11.64-12.79 (m, 1H). MS ES+ m/z 391 [M+H]+.

Example 53

Methyl N-[4-[2-tert-butoxy-6-[1-ethyl-3-(trifluoromethyl)pyrazol-4-yl]-4-pyridyl]-2-pyridyl]carbamate

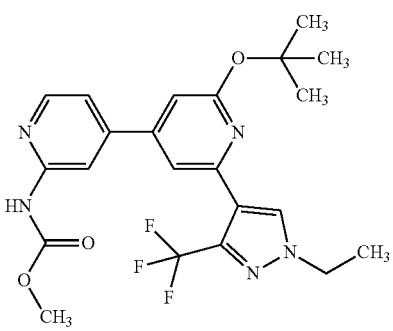 [SMILES: CCn1cc(-c2cc(-c3ccnc(NC(=O)OC)c3)cc(OC(C)(C)C)n2)c(C(F)(F)F)n1]

The title compound was prepared as described in Example 33, using methyl N-[4-(2-tert-butoxy-6-chloro-4-pyridyl)-2-pyridyl]carbamate and 1-ethyl-3-(trifluoromethyl)pyrazol-4-yl]boronic acid, to give the product as a solid (130 mg, 94%). MS ES+ m/z 464 [M+H]+.

Example 54

Methyl N-[4-[2-[1-ethyl-3-(trifluoromethyl)pyrazol-4-yl]-6-oxo-1H-pyridin-4-yl]-2-pyridyl]carbamate

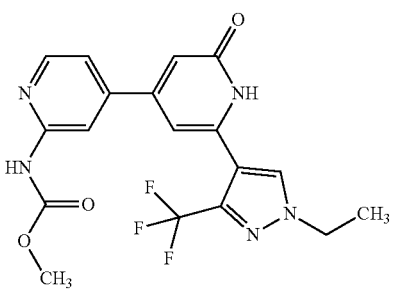 [SMILES: CCn1cc(-c2cc(-c3ccnc(NC(=O)OC)c3)cc(=O)[nH]2)c(C(F)(F)F)n1]

The title compound was prepared as described in Example 30, to give the product as a solid (6 mg, 5%). $^1$H NMR (500 MHz, DMSO-$d_6$) δ ppm 1.46 (t, 3H), 3.71 (s, 3H), 4.29 (q, 2H), 6.71 (br s, 2H), 7.36 (dd, 1H), 8.11 (s, 1H), 8.38 (d, 1H), 8.44 (s, 1H), 10.37 (s, 1H), 11.7 (br s, 1H). MS ES+ m/z 408 [M+H]+.

Example 55

4-Benzyloxy-2-tert-butoxy-6-[2-(trifluoromethyl)phenyl]pyridine

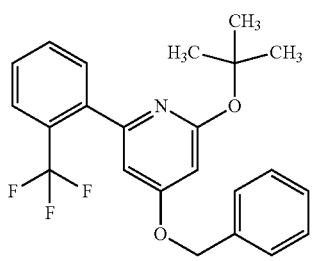 [SMILES: CC(C)(C)Oc1cc(OCc2ccccc2)cc(-c2ccccc2C(F)(F)F)n1]

4-Benzyloxy-2-tert-butoxy-6-chloro-pyridine (1.46 g, 5 mmol), [2-(trifluoromethyl)phenyl]boronic acid (950 mg, 5 mmol), K$_2$CO$_3$ (1.73 g, 12.5 mmol) and PdCl$_2$ (dppf) (366 mg, 0.5 mmol) were dissolved in 1,4-dioxane (25 ml) and water (5 ml) and the resulting mixture was stirred at 90° C. for 2 h. When cooled to rt the mixture was diluted with water and EtOAc. The organic layer was separated and the aqueous layer extracted with EtOAc. The combined organics were filtered through celite, dried over Na$_2$SO$_4$, filtered, concentrated and purified on a silica gel column eluted with 0-80% EtOAc in heptane to give the product as a solid (1.58 g, 79%). MS ES+ m/z 402 [M+H]+.

Example 56

2-tert-Butoxy-6-[2-(trifluoromethyl)phenyl]pyridin-4-ol

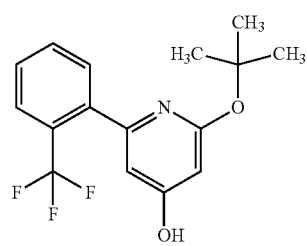 [SMILES: CC(C)(C)Oc1cc(O)cc(-c2ccccc2C(F)(F)F)n1]

The title compound was prepared as described in Example 16 to give the product (948 mg, 72%). MS ES+ m/z 312 [M+H]+.

Example 57

[2-tert-Butoxy-6-[2-(trifluoromethyl)phenyl]-4-pyridyl]trifluoromethanesulfonate

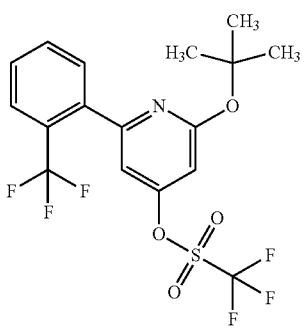 [SMILES: CC(C)(C)Oc1cc(OS(=O)(=O)C(F)(F)F)cc(-c2ccccc2C(F)(F)F)n1]

The title compound was prepared as described in Example 17 to give the product (720 mg, 54%). MS ES+ m/z 388 [M-tBu]+.

Example 58

2-tert-Butoxy-4-(4,4,5,5-tetramethyl-1,3,2-dioxaborolan-2-yl)-6-[2-(trifluoromethyl)phenyl]pyridine

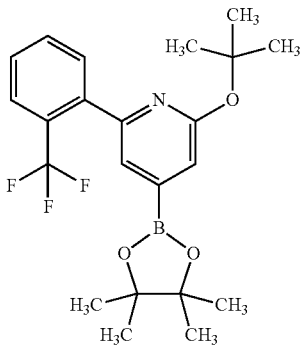 [SMILES: CC(C)(C)Oc1cc(B2OC(C)(C)C(C)(C)O2)cc(-c2ccccc2C(F)(F)F)n1]

The title compound was prepared as described in Example 18 to give the product (450 mg, 76%). MS ES+ m/z 340 [M+H]+ (boronic acid).

Example 59

Phenyl N-(4-chloro-2-pyridyl)-N-phenoxycarbonyl-carbamate

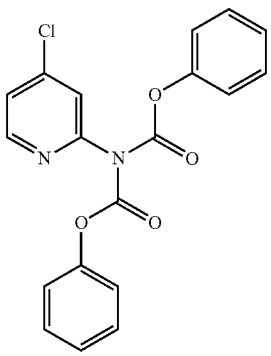 [SMILES: O=C(Oc1ccccc1)N(C(=O)Oc1ccccc1)c1cc(Cl)ccn1]

Phenyl chloroformate (0.94 ml, 7.5 mmol) was added slowly to a solution of 4-chloropyridin-2-amine (386 mg, 3 mmol) and TEA (1.25 ml, 9 mmol) in DCM (15 ml) at 0° C. and the resulting mixture was stirred at rt for 2 h. DCM and MeOH were added and the mixture poured into sat. aq. NaHCO$_3$. After being stirred for 15 min the organic layer was separated. The aqueous layer was extracted with DCM and the combined organics were dried over Na$_2$SO$_4$, filtered, concentrated and purified on a silica gel column eluted with 0-80% EtOAc in heptane to give the product as a solid (1.1 g, 99%). MS ES+ m/z 369 [M+H]+.

Example 60

3-(4-Chloro-2-pyridyl)-1,1-dimethyl-urea

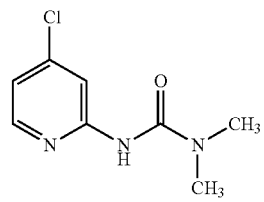

Aq. 40% dimethylamine (1.9 ml, 15 mmol) was added to a solution of phenyl N-(4-chloro-2-pyridyl)-N-phenoxycarbonyl-carbamate (1.1 g, 3 mmol) in THF (15 ml) and the resulting mixture was stirred at rt overnight. Water was added, and the mixture was extracted with EtOAc. The combined organics were dried over Na$_2$SO$_4$, filtered, concentrated and purified on a silica gel column eluted with 0-60% EtOAc in DCM to give the product as a solid (420 mg, 70%). MS ES+ m/z 200 [M+H]+.

Example 61

3-[4-[2-tert-Butoxy-6-[2-(trifluoromethyl)phenyl]-4-pyridyl]-2-pyridyl]-1,1-dimethyl-urea

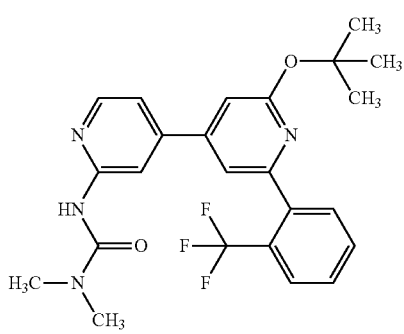 [SMILES: CN(C)C(=O)Nc1cc(-c2cc(OC(C)(C)C)nc(-c3ccccc3C(F)(F)F)c2)ccn1]

The title compound was prepared as described in Example 20, using 2-tert-butoxy-4-(4,4,5,5-tetramethyl-1,3,2-dioxaborolan-2-yl)-6-[2-(trifluoromethyl)phenyl]pyridine and 3-(4-chloro-2-pyridyl)-1,1-dimethyl-urea, to give the product as a solid (140 mg, 51%). MS ES+ m/z 459 [M+H]$^+$.

Example 62

1,1-Dimethyl-3-[4-[2-oxo-6-[2-(trifluoromethyl)phenyl]-1H-pyridin-4-yl]-2-pyridyl]urea

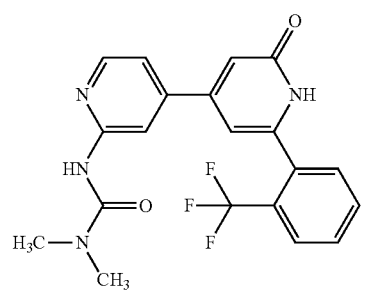 [SMILES: CN(C)C(=O)Nc1cc(-c2cc(-c3ccccc3C(F)(F)F)[nH]c(=O)c2)ccn1]

The title compound was prepared as described in Example 30, to give the product as a solid (28 mg, 47%). $^1$H NMR (500 MHz, DMSO-d$_6$) δ ppm 2.92-3.03 (m, 6H), 6.51 (br s, 1H), 6.74 (s, 1H), 7.31 (dd, 1H), 7.64-7.85 (m, 2H), 7.89 (d, 1H), 8.11 (s, 1H), 8.33 (d, 1H), 9.02 (s, 1H), 10.82-12.57 (m, 2H). MS ES+ m/z 403 [M+H]$^+$.

Example 63

4-Hydroxy-6-[2-(trifluoromethyl)phenyl]-1H-pyridin-2-one

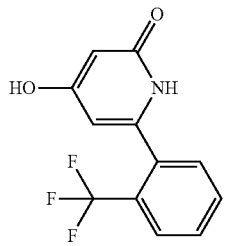 [SMILES: O=c1cc(O)cc(-c2ccccc2C(F)(F)F)[nH]1]

The title compound was prepared as described in Example 6, to give the product as a solid (2.3 g, 18%). MS ES+ m/z 256 [M+H]$^+$.

Example 64

2,4-Dichloro-6-[2-(trifluoromethyl)phenyl]pyridine

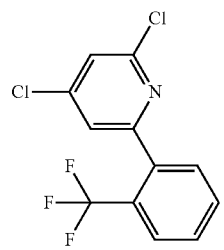 [SMILES: FC(F)(F)c1ccccc1-c1cc(Cl)cc(Cl)n1]

The title compound was prepared as described in Example 7, to give the product as a solid (1.9 g, 72%). MS ES+ m/z 292 [M+H]$^+$.

Example 65

4-Chloro-6-[2-(trifluoromethyl)phenyl]-1H-pyridin-2-one

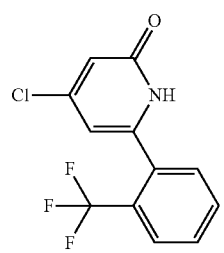 [SMILES: O=c1cc(Cl)cc(-c2ccccc2C(F)(F)F)[nH]1]

The title compound was prepared as described in Example 8, except the TFA solution was neutralized using solid NaHCO$_3$ and extracted with DCM. The combined organics were dried over Na$_2$SO$_4$, filtered and concentrated. Recrystallization from Et$_2$O gave the product as a solid (2.05 g, 80%). MS ES+ m/z 274 [M+H]$^+$.

Example 66

N-[4-[2-oxo-6-[2-(trifluoromethyl)phenyl]-1H-pyridin-4-yl]-2-pyridyl]pyrrolidine-1-carboxamide

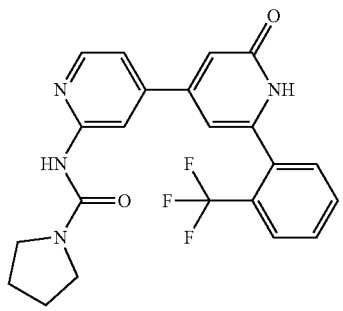 [SMILES: O=C(Nc1cc(-c2cc(-c3ccccc3C(F)(F)F)[nH]c(=O)c2)ccn1)N1CCCC1]

To an ice cooled suspension of 4-(4,4,5,5-tetramethyl-1,3,2-dioxaborolan-2-yl)pyridin-2-amine (550 mg, 2.50 mmol) in DCM (10 ml) and THF (5 ml) was added TEA (1.05 ml, 7.50 mmol) and then dropwise phenyl chloroformate (783 mg, 5 mmol). The cooling bath was removed and the resulting mixture was stirred at rt overnight. Pyrrolidine (889 mg, 12.5 mmol) was added and the reaction was stirred at rt for 20 h. The mixture was added to water and EtOAc. The aqueous layer was separated and concentrated to give the crude boronic acid, which was taken up in 1,4-dioxane (2.5 ml) and water (0.5 ml). 4-chloro-6-[2-(trifluoromethyl)phenyl]-1H-pyridin-2-one (68 mg, 0.25 mmol), K$_2$CO$_3$ (69 mg, 0.5 mmol) and PdCl$_2$(dppf) (27 mg, 0.04 mmol) were added and the resulting mixture was heated and stirred at 90° C. for 8 h. When cooled to rt, the mixture was diluted with 1,4-dioxane, filtered through celite, concentrated and purified by preparative HPLC to give the product as a solid (30 mg, 28%). $^1$H NMR (500 MHz, DMSO-d$_6$) δ ppm 1.85 (br s, 4H), 3.41 (br s, 4H), 6.51 (br s, 1H), 6.74 (s, 1H), 7.32 (dd, 1H), 7.66 (d, 1H), 7.71-7.82 (m, 2H), 7.89 (d, 1H), 8.21 (s, 1H), 8.33 (d, 1H), 8.83 (s, 1H), 12.08 (br s, 1H). MS ES+ m/z 429 [M+H]$^+$.

Example 67

N-[4-[2-tert-butoxy-6-[2-(1-methoxy-1-methyl-ethyl)pyrrolidin in-1-yl]-4-pyridyl]-2-pyridyl]acetamide

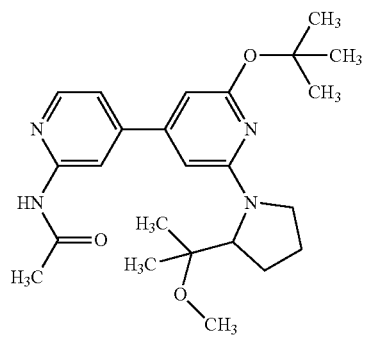 [SMILES: COC(C)(C)C1CCCN1c1cc(-c2ccnc(NC(C)=O)c2)cc(OC(C)(C)C)n1]

N-[4-(2-tert-butoxy-6-chloro-4-pyridyl)-2-pyridyl]acetamide (128 mg, 0.4 mmol), 2-(1-methoxy-1-methyl-ethyl)pyrrolidine (86 mg, 0.6 mmol), PEPPSI-iPr (14 mg, 0.02 mmol) and KOtBu (99 mg, 0.88 mmol) were taken up in 1,4-dioxane (3 ml) and the mixture was stirred at 80° C. overnight. Additional KOtBu (49 mg, 0.44 mmol) and PEPPSI-iPr (7 mg, 0.01 mmol) were added and the mixture was stirred at 90° C. for 6 h. When cooled to rt aq. 10% NaCl was added and the mixture extracted with EtOAc. The combined organics were dried over Na$_2$SO$_4$, filtered, concentrated and purified on a silica gel column eluted with 0-80% EtOAc in heptane to give the product as a solid (46 mg, 27%). MS ES+ m/z 427 [M+H]$^+$.

Example 68

N-[4-[2-[2-(1-methoxy-1-methyl-ethyl)pyrrolidin-1-yl]-6-oxo-1H-pyridin-4-yl]-2-pyridyl]acetamide

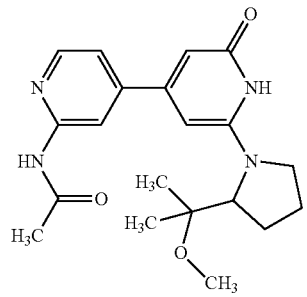 [SMILES: COC(C)(C)C1CCCN1c1cc(-c2ccnc(NC(C)=O)c2)cc(=O)[nH]1]

The title compound was prepared as described in Example 30, to give the product as a solid (16 mg, 41%). $^1$H NMR (500 MHz, DMSO-d$_6$) δ ppm 1.12 (s, 3H), 1.17 (br s, 3H), 1.81-1.92 (m, 2H), 1.98 (br d, 3H), 2.12 (s, 3H), 3.19 (s, 3H), 3.39-3.52 (m, 2H), 5.77 (s, 1H), 5.86 (br s, 1H), 7.33 (dd, 1H), 8.32 (s, 1H), 8.36 (d, 1H), 10.60 (s, 1H), 10.67-11.27 (m, 1H). MS ES+ m/z 371 [M+H]$^+$.

Example 69

Methyl N-[4-[2-tert-butoxy-6-[2-(trifluoromethyl)-1-piperidyl]-4-pyridyl]-2-pyridyl]carbamate

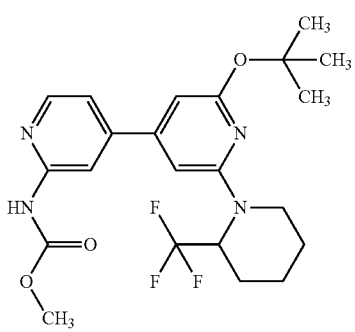 [SMILES: COC(=O)Nc1cc(-c2cc(OC(C)(C)C)nc(N3CCCCC3C(F)(F)F)c2)ccn1]

Methyl carbonochloridate (66 μl, 0.86 mmol) was added slowly to a solution of 4-[2-tert-butoxy-6-[2-(trifluoromethyl)-1-piperidyl]-4-pyridyl]pyridin-2-amine (135 mg, 0.34 mmol) and N,N-diisopropylethylamine (0.3 ml, 1.71 mmol) in DCM (15 ml) at 0° C. The resulting mixture was stirred at 0° C. for 30 minutes, MeOH was added and the mixture was concentrated. The resulting residue was dissolved in MeOH (10 ml), aq. 1M NaOH (2 ml) was added and the mixture was stirred at rt for 2.5 h. Water was added and the mixture was extracted with EtOAc. The combined organics were washed with brine, dried over $Na_2SO_4$, filtered, concentrated and purified on a silica gel column eluted with 0-80% EtOAc in heptane to give the product as a solid (150 mg, 88%). MS ES+ m/z 453 [M+H]$^+$.

Example 70

Methyl N-[4-[2-oxo-6-[2-(trifluoromethyl)-1-piperidyl]-1H-pyridin-4-yl]-2-pyridyl]carbamate

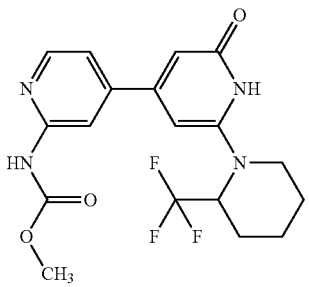

The title compound was prepared as described in Example 30, to give the product as a solid (36 mg, 41%). $^1$H NMR (500 MHz, DMSO-d$_6$) δ ppm 1.35-1.54 (m, 1H), 1.61-1.70 (m, 2H), 1.70-1.83 (m, 2H), 1.99 (br d, 1H), 3.04 (br t, 1H), 3.70 (s, 3H), 4.17 (br d, 1H), 5.51-5.62 (m, 1H), 6.18 (s, 1H), 6.50 (br s, 1H), 7.37 (dd, 1H), 8.06-8.09 (m, 1H), 8.33 (dd, 1H), 10.29 (br s, 2H). MS ES+ m/z 397 [M+H]$^+$.

Example 71

Vps34 Biochemical Assay

Dilution series of compounds of the invention were prepared in DMSO at 100 times the final assay concentration ($n_1=n_0/3$ in 10 points). The compounds were further diluted to 4 times the assay concentration in assay buffer (Life technologies buffer Q, PV5125, diluted 5 times supplemented with 2 mM DTT and 2 mM $MnCl_2$). 2.5 µl of the diluted compounds were added to a 384 well assay plate followed by 2.5 µl of 16.5 nM Vps34 enzyme (Life technologies, PV5126). Enzyme and compounds were pre-incubated at rt for 15 min. Then 5 µl of substrate mix containing 20 µM ATP (Life technologies, PV3227) and 200 µM PI:PS substrate (Life technologies, PV5122) in assay buffer was added to the wells containing compound and enzyme. Mixing was performed by pipetting several times. The reaction was incubated at room temperature for 1 h. Then 5 µl stop-detection mix, prepared as described in the Adapta kinase assay kit instructions (Life technologies, PV5099) containing Adapta Eu-anti-ADP antibody (2.3 nM), Alexa Fluor 647 ADP tracer (9 nM) and EDTA (30 mM) in TR-FRET buffer, was added to quench the reaction. Mixing was performed by pipetting several times. The assay plate was then incubated at room temperature for 30 min and read with Artemis micro plate reader. Percent inhibition of the compounds as compared to DMSO treated control samples was calculated. By the use of Dotmatics software compound concentration versus percent inhibition was fitted to generate $IC_{50}$ values.

The example compounds effectively inhibited Vps34 and the results of the assay are shown in Table 1 (Median $IC_{50}$ nM Adapta).

TABLE 1

| Median $IC_{50}$ values for the Vps34 assay | |
|---|---|
| Example Compound | Median IC50 nM Adapta |
| 1 | <5 |
| 5 | 410 |
| 11 | 45 |
| 12 | 7 |
| 19 | 12 |
| 21 | <5 |
| 26 | <5 |
| 30 | <5 |
| 32 | 5 |
| 34 | <5 |
| 36 | <5 |
| 38 | <5 |
| 40 | <5 |
| 42 | <5 |
| 44 | <5 |
| 45 | <5 |
| 48 | <5 |
| 50 | <5 |
| 52 | <5 |
| 54 | <5 |
| 62 | 50 |
| 66 | 147 |
| 68 | 26 |
| 70 | <5 |

Example 72

High Content Screening Autophagy Assay

Human osteosarcoma cells (HOS) stably expressing a Green Fluorescent Protein (GFP) tagged LC3 (GFP-LC3) were used to determine the inhibitory effect on autophagy of proprietary compounds. For that purpose, autophagy was activated by using the mTOR inhibitor KU-0063794 at 500 nM in the presence of Bafilomycin A1 (Sigma-Aldrich) at 5 nM. Shortly, cells were plated overnight in clear bottom 96-well plates in DMEM—High Modified media (Hi-Clone Cat #SH30285.01). At the start of the experiment, the media was removed and replaced with fresh media containing the mTOR inhibitor, Bafilomycin A1 and the vehicle or a test compound as indicated. After 6 hours the media was removed, cells were washed twice with ice-cold phosphate buffered saline (PBS) and fixed with 4% paraformaldehyde for 20 minutes at room temperature. Then the cells were washed twice with ice-cold PBS before adding Hoechst 33342 at 1 µg/ml in PBS for nuclear staining. After incubation overnight at 4° C., cells were washed once with PBS to remove the excess of dye and 100 µl of PBS was added to each well. Images were acquired at 20× magnification, 6 images per well, using the ImageXpress automated microscope (Molecular Devices Inc.) and analyzed with MetaXpress software to identify LC3-GFP foci. Foci area per cell values were used to generate dose response curves and 1050 values were calculated using the non-linear fitting analysis in GraphPad Prism software.

The tested example compounds effectively inhibited autophagy in HOS cells. The results of the assay are shown in Table 2 (Median IC$_{50}$ μM HOS-LC3).

TABLE 2

Median IC$_{50}$ values for the Vps34 assay and autophagy in HOS cells assay.

| Example Compound | Median IC50 (μM) Cellular assay |
|---|---|
| 1 | 0.026 |
| 11 | 0.742 |
| 12 | 0.147 |
| 19 | 0.067 |
| 21 | 0.016 |
| 26 | 0.113 |
| 30 | 0.020 |
| 34 | 0.063 |
| 36 | 0.092 |
| 42 | 0.046 |
| 44 | 0.138 |
| 45 | 0.023 |
| 48 | 0.020 |
| 50 | 0.029 |
| 52 | 0.022 |
| 54 | 0.105 |

The following compounds are synthesized using suitable changes of starting material, and if necessary customizations of reaction conditions and the like:

methyl N-[4-[2-(4-methyl-3-pyridyl)-6-oxo-1H-pyridin-4-yl]-2-pyridyl]carbamate;

methyl N-[4-[2-[4-ethylsulfonyl-2-(trifluoromethyl)piperazin-1-yl]-6-oxo-1H-pyridin-4-yl]-2-pyridyl]carbamate;

methyl N-[4-[2-(3-cyclopropylmorpholin-4-yl)-6-oxo-1H-pyridin-4-yl]-2-pyridyl]carbamate;

3-[4-[2-(2-chlorophenyl)-6-oxo-1H-pyridin-4-yl]-2-pyridyl]-1,1-dimethyl-urea; and N-[4-[2-(2-chlorophenyl)-6-oxo-1H-pyridin-4-yl]-2-pyridyl]pyrrolidine-1-carboxamide.

The invention claimed is:

1. A compound of formula (I)

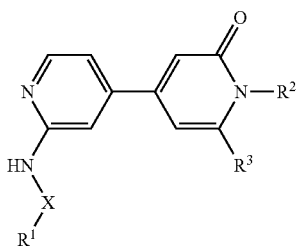

wherein
X is C=O or a bond;
R$^1$ is selected from H, C$_1$-C$_3$alkyl, C$_1$-C$_3$haloalkyl, C$_1$-C$_3$alkoxyC$_1$-C$_3$alkyl, C$_3$-C$_6$cycloalkyl, C$_3$-C$_6$cyclohaloalkyl, C$_1$-C$_3$alkoxy, C$_1$-C$_3$haloalkoxy, C$_3$-C$_6$cycloalkoxymethyl, N—C$_1$-C$_3$alkylamino, N,N-diC$_1$-C$_3$alkylamino, 1-pyrrolidinyl, 1-piperidinyl and 1-azetidinyl, provided that when R$^1$ is C$_1$-C$_3$alkoxy, C$_1$-C$_3$haloalkoxy, N—C$_1$-C$_3$alkylamino N,N-diC$_1$-C$_3$alkylamino, 1-pyrrolidinyl, 1-piperidinyl or 1-azetidinyl, then X is C=O;
R$^2$ is selected from hydrogen, C$_1$-C$_3$haloalkyl and C$_1$-C$_3$alkyl;
R$^3$ is selected from A, phenyl and monocyclic heteroaryl, said phenyl and said heteroaryl being optionally substituted with one or more of R$^4$, R$^5$, R$^6$ and R$^7$;
R$^4$, R$^5$, R$^6$ and R$^7$ are independently selected from halo, C$_1$-C$_6$alkyl, C$_3$-C$_6$cycloalkyl, C$_1$-C$_6$alkoxy, C$_1$-C$_3$haloalkoxy, N,N-diC$_1$-C$_3$alkylamino, N—C$_1$-C$_3$alkylamino, 1-azetidinyl, C$_1$-C$_6$haloalkyl, amino, NHSO$_2$R$^8$, SO$_2$R$^9$ and hydroxy;
R$^8$ is C$_1$-C$_3$haloalkyl or C$_1$-C$_3$alkyl;
R$^9$ is selected from R$^{10}$, C$_1$-C$_6$alkyl, amino, N—C$_1$-C$_3$alkylamino, N,N-diC$_1$-C$_3$alkylamino and C$_1$-C$_3$alkoxyC$_1$-C$_3$alkyl, said C$_1$-C$_6$alkyl and said C$_1$-C$_3$alkoxyC$_1$-C$_3$alkyl being optionally substituted with one R$^{10}$ and/or one or more halo;
R$^{10}$ is selected from phenyl, monocyclic heteroaryl, C$_3$-C$_6$cycloalkyl, heterocyclyl, each optionally substituted with one or more R$^{11}$;
R$^{11}$ is selected from halo, C$_1$-C$_3$alkoxyC$_1$-C$_3$alkyl, amino, N—C$_1$-C$_3$alkylamino, N,N-diC$_1$-C$_3$alkylamino, C$_1$-C$_3$haloalkoxy, C$_1$-C$_3$alkoxy, C$_3$-C$_6$cycloalkyl, C$_1$-C$_3$haloalkyl and C$_1$-C$_3$alkyl;
A represents

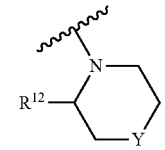

R$^{12}$ is selected from hydrogen, halo, COR$^{13}$, C$_1$-C$_6$alkyl, C$_1$-C$_3$alkoxyC$_1$-C$_3$alkyl, C$_1$-C$_6$alkoxy, C$_3$-C$_6$cycloalkyl, C$_1$-C$_3$cyanoalkyl, C$_1$-C$_3$haloalkyl;
R$^{13}$ is selected from C$_1$-C$_3$alkoxy, N—C$_1$-C$_3$alkylamino, N,N-diC$_1$-C$_3$alkylamino, 1-pyrrolidinyl, 1-piperidinyl and 1-azetidinyl;
Y represents CH$_2$, S, SO, SO$_2$, NR$^{14}$, NCOR$^9$, NCOOR$^{15}$, NSO$_2$R$^9$, NCOCH$_2$R$^9$, O, or a bond;
R$^{14}$ is selected from H, C$_1$-C$_3$haloalkyl, C$_1$-C$_3$alkoxyC$_1$-C$_3$alkyl, C$_1$-C$_3$alkyl, C$_3$-C$_6$cycloalkyl;
R$^{15}$ is selected from R$^{10}$, C$_1$-C$_6$alkyl and C$_1$-C$_3$alkoxyC$_1$-C$_3$alkyl, said C$_1$-C$_6$alkyl and said C$_1$-C$_3$alkoxyC$_1$-C$_3$alkyl being optionally substituted with one R$^{10}$ and/or one or more halo;
or a pharmaceutically acceptable salt thereof.

2. The compound according to claim 1, wherein R$^2$ is hydrogen or C$_1$-C$_3$alkyl;
or a pharmaceutically acceptable salt thereof.

3. The compound according to claim 1, wherein R$^1$ is selected from H, C$_1$-C$_3$alkyl, C$_1$-C$_3$alkoxy, C$_1$-C$_3$haloalkoxy, C$_1$-C$_3$alkoxyC$_1$-C$_3$alkyl, N,N-diC$_1$-C$_3$alkylamino, 1-pyrrolidinyl and C$_3$-C$_6$cycloalkyl;
or a pharmaceutically acceptable salt thereof.

4. The compound according to claim 1, wherein R$^1$ is selected from H, methyl, methoxy, methoxymethyl, N,N-dimethylamino, 1-pyrrolidinyl and cyclopropyl;
or a pharmaceutically acceptable salt thereof.

5. The compound according to claim 1, wherein R$^1$ is selected from H, methyl, methoxymethyl, N,N-dimethylamino, 1-pyrrolidinyl and cyclopropyl;
or a pharmaceutically acceptable salt thereof.

6. The compound according to claim 1, wherein $R^3$ is selected from A, phenyl and monocyclic heteroaryl selected from pyridyl, thienyl, furyl, pyrimidinyl and pyrazolyl, wherein said phenyl and said heteroaryl are optionally substituted with $R^4$ and/or $R^5$;

or a pharmaceutically acceptable salt thereof.

7. The compound according to claim 1, wherein $R^4$, $R^5$, $R^6$ and $R^7$ are independently selected from fluoro, chloro, $C_1$-$C_3$alkyl, $C_3$-$C_6$cycloalkyl, $C_1$-$C_3$fluoroalkyl and $SO_2R^9$;

or a pharmaceutically acceptable salt thereof.

8. The compound according to claim 1, wherein $R^{12}$ is selected from hydrogen, $C_1$-$C_3$alkyl, $C_1$-$C_3$alkoxy$C_1$-$C_3$alkyl, $C_1$-$C_3$haloalkyl and $C_3$-$C_6$cycloalkyl;

or a pharmaceutically acceptable salt thereof.

9. The compound according to claim 1, wherein $R^9$ is selected from $R^{10}$, N,N-di$C_1$-$C_3$alkylamino and methoxy$C_1$-$C_3$alkyl, said $C_1$-$C_3$alkyl being optionally substituted with one $R^{10}$;

or a pharmaceutically acceptable salt thereof.

10. The compound according to claim 1, wherein $R^{10}$ is selected from phenyl, pyridyl, imidazolyl, isoxazolyl, oxazolyl, cyclopropyl, cyclopentyl, pyrrolidinyl, tetrahydrofuryl, each optionally substituted with one or more methyl and/or fluoro;

or a pharmaceutically acceptable salt thereof.

11. The compound according to claim 1, wherein $R^3$ is selected from

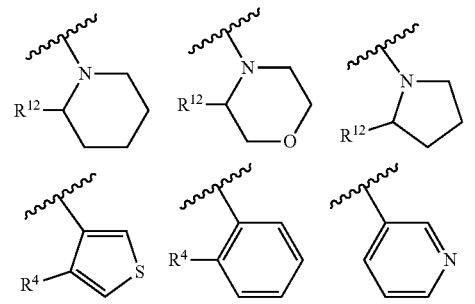

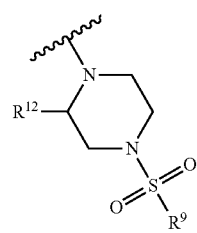

or a pharmaceutically acceptable salt thereof.

12. The compound according to claim 1, wherein $R^3$ is selected from

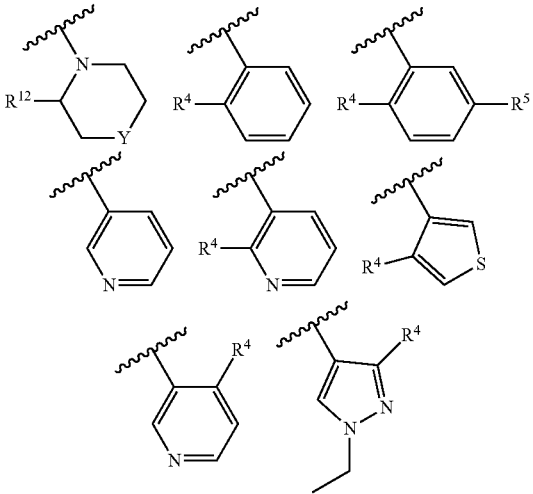

wherein Y is selected from $CH_2$, O and a bond;

$R^4$ is selected from CF3, chloro, cyclopropyl and methyl;

R5 is fluoro; and

R12 is selected from hydrogen, cyclopropyl, methyl, 1-methoxy-1-methyl-ethyl and CF3;

or a pharmaceutically acceptable salt thereof.

13. The compound according to claim 1, wherein

R1 is selected from H, methyl, methoxy, methoxymethyl, N,N-dimethylamino, 1-pyrrolidinyl and cyclopropyl;

R2 is hydrogen; and

R3 is selected from

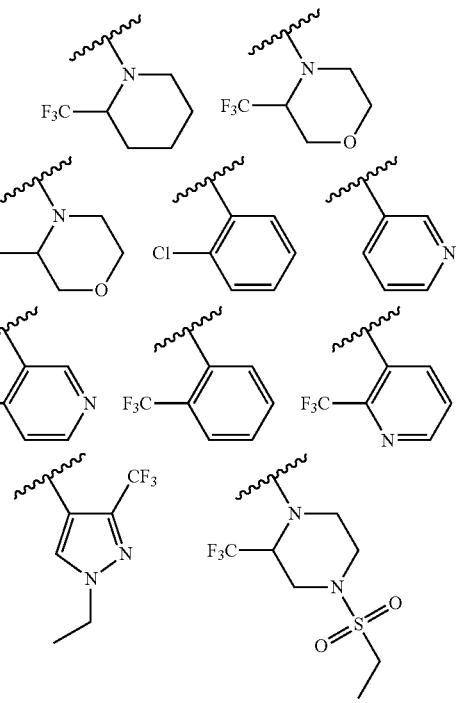

-continued

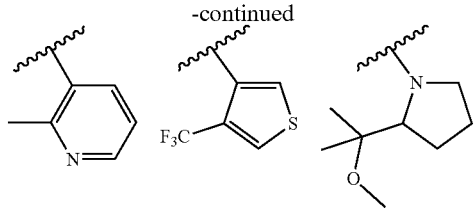

or a pharmaceutically acceptable salt thereof.

14. The compound according to claim 1, wherein
 $R^1$ is selected from H, methyl, methoxy, methoxymethyl, N,N-dimethylamino, 1-pyrrolidinyl and cyclopropyl;
 $R^2$ is hydrogen; and
 $R^3$ is selected from

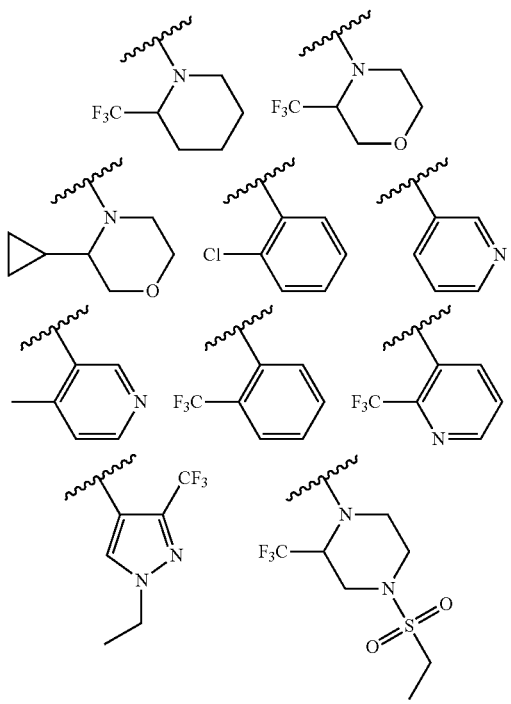

or a pharmaceutically acceptable salt thereof.

15. The compound according to claim 1, said compound being
 N-[4-[2-(2-chlorophenyl)-6-oxo-1H-pyridin-4-yl]-2-pyridyl]acetamide;
 4-(2-Amino-4-pyridyl)-6-(3-pyridyl)-1H-pyridin-2-one;
 4-(2-Amino-4-pyridyl)-6-(2-chlorophenyl)-1H-pyridin-2-one;
 N-[4-[2-(2-chlorophenyl)-6-oxo-1H-pyridin-4-yl]-2-pyridyl]-2-methoxy-acetamide;
 N-[4-[2-oxo-6-[2-(trifluoromethyl)-1-piperidyl]-1H-pyridin-4-yl]-2-pyridyl]acetamide;
 N-[4-[2-oxo-6-[2-(trifluoromethyl)-1-piperidyl]-1H-pyridin-4-yl]-2-pyridyl]cyclopropanecarboxamide;
 N-[4-[2-oxo-6-[3-(trifluoromethyl)morpholin-4-yl]-1H-pyridin-4-yl]-2-pyridyl]acetamide;
 methyl N-[4-[2-(2-chlorophenyl)-6-oxo-1H-pyridin-4-yl]-2-pyridyl]carbamate;
 methyl N-[4-[2-[1-ethyl-3-(trifluoromethyl)pyrazol-4-yl]-6-oxo-1H-pyridin-4-yl]-2-pyridyl]carbamate;
 methyl N-[4-[2-oxo-6-[2-(trifluoromethyl)-3-pyridyl]-1H-pyridin-4-yl]-2-pyridyl]carbamate;
 methyl N-[4-[2-oxo-6-[2-(trifluoromethyl)phenyl]-1H-pyridin-4-yl]-2-pyridyl]carbamate;
 N-[4-[2-oxo-6-[2-(trifluoromethyl)phenyl]-1H-pyridin-4-yl]-2-pyridyl]acetamide;
 N-[4-[2-(4-methyl-3-pyridyl)-6-oxo-1H-pyridin-4-yl]-2-pyridyl]acetamide;
 N-[4-[2-oxo-6-[2-(trifluoromethyl)-3-pyridyl]-1H-pyridin-4-yl]-2-pyridyl]acetamide;
 N-[4-[2-[1-ethyl-3-(trifluoromethyl)pyrazol-4-yl]-6-oxo-1H-pyridin-4-yl]-2-pyridyl]acetamide;
 methyl N-[4-[2-oxo-6-[3-(trifluoromethyl)morpholin-4-yl]-1H-pyridin-4-yl]-2-pyridyl]carbamate;
 methyl N-[4-[2-oxo-6-[2-(trifluoromethyl)-1-piperidyl]-1H-pyridin-4-yl]-2-pyridyl]carbamate;
 N-[4-[2-(3-cyclopropylmorpholin-4-yl)-6-oxo-1H-pyridin-4-yl]-2-pyridyl]acetamide;
 N-[4-[2-[4-ethylsulfonyl-2-(trifluoromethyl)piperazin-1-yl]-6-oxo-1H-pyridin-4-yl]-2-pyridyl]acetamide;
 N-[4-[2-(2-methyl-3-pyridyl)-6-oxo-1H-pyridin-4-yl]-2-pyridyl]acetamide;
 N-[4-[2-oxo-6-[4-(trifluoromethyl)-3-thienyl]-1H-pyridin-4-yl]-2-pyridyl]acetamide;
 1,1-Dimethyl-3-[4-[2-oxo-6-[2-(trifluoromethyl)phenyl]-1H-pyridin-4-yl]-2-pyridyl]urea;
 N-[4-[2-oxo-6-[2-(trifluoromethyl)phenyl]-1H-pyridin-4-yl]-2-pyridyl]pyrrolidine-1-carboxamide;
 N-[4-[2-[2-(1-methoxy-1-methyl-ethyl)pyrrolidin-1-yl]-6-oxo-1H-pyridin-4-yl]-2-pyridyl]acetamide;
 or a pharmaceutically acceptable salt thereof.

16. A pharmaceutical composition comprising a compound according to claim 1, or a pharmaceutically acceptable salt thereof, and a pharmaceutically acceptable diluent, carrier and/or excipient.

17. A pharmaceutical composition, comprising a therapeutically effective amount of a compound according to claim 1, or a pharmaceutically acceptable salt thereof, and another anticancer agent selected from alkylating agents, antimetabolites, anticancer camptothecin derivatives, plant-derived anticancer agents, antibiotics, enzymes, platinum coordination complexes, tyrosine kinase inhibitors, hormones, hormone antagonists, monoclonal antibodies, interferons, and biological response modifiers.

* * * * *